United States Patent
Udayampalayam Palanisamy et al.

(10) Patent No.: US 10,201,532 B2
(45) Date of Patent: Feb. 12, 2019

(54) COMPOUNDS AND THEIR USE

(75) Inventors: Senthilkumar Udayampalayam Palanisamy, Chennai (IN); Maneesh Paul-Satyaseela, Chennai (IN); Shridhar Narayanan, Chennai (IN); Gopalan Balasubramanian, Chennai (IN); Aravind Appu, Chennai (IN); Senthilnathan Manickam, Chennai (IN); Hariharan Periasamy, Chennai (IN)

(73) Assignee: ALLECRA THERAPEUTICS GMBH, Lorrach (DE)

(*) Notice: Subject to any disclaimer, the term of this patent is extended or adjusted under 35 U.S.C. 154(b) by 625 days.

(21) Appl. No.: 13/989,600

(22) PCT Filed: Nov. 25, 2011

(86) PCT No.: PCT/IN2011/000813
§ 371 (c)(1),
(2), (4) Date: Nov. 12, 2013

(87) PCT Pub. No.: WO2012/070071
PCT Pub. Date: May 31, 2012

(65) Prior Publication Data
US 2014/0057888 A1    Feb. 27, 2014

(30) Foreign Application Priority Data

Nov. 25, 2010  (IN) .......................... 3555/CHE/2010
Sep. 9, 2011   (IN) .......................... 3096/CHE/2011

(51) Int. Cl.
| | |
|---|---|
| A61K 31/431 | (2006.01) |
| C07D 499/883 | (2006.01) |
| A61K 31/397 | (2006.01) |
| A61K 31/4025 | (2006.01) |
| A61K 31/496 | (2006.01) |
| A61K 31/542 | (2006.01) |
| C07D 499/00 | (2006.01) |
| C12Q 1/44 | (2006.01) |

(52) U.S. Cl.
CPC .......... *A61K 31/431* (2013.01); *A61K 31/397* (2013.01); *A61K 31/4025* (2013.01); *A61K 31/496* (2013.01); *A61K 31/542* (2013.01); *C07D 499/00* (2013.01); *C07D 499/883* (2013.01); *C12Q 1/44* (2013.01)

(58) Field of Classification Search
CPC ................................................. A61K 31/431
See application file for complete search history.

(56) References Cited

U.S. PATENT DOCUMENTS

| | | | |
|---|---|---|---|
| 4,562,073 A | 12/1985 | Micetich et al. | |
| 4,891,369 A | 1/1990 | Torii et al. | |
| 7,687,488 B2 | 3/2010 | Udayampalayam Palanisamy et al. | |
| 2006/0084639 A1 | 4/2006 | Cohen et al. | |
| 2008/0015156 A1* | 1/2008 | Udayampalayam Palanisamy et al. .............. | 514/40 |
| 2010/0092443 A1 | 4/2010 | Levasseur et al. | |
| 2011/0166091 A1 | 7/2011 | Cohen et al. | |

FOREIGN PATENT DOCUMENTS

| | | |
|---|---|---|
| JP | S39-006283 | 1/1989 |
| MX | 2011003812 A | 7/2011 |

OTHER PUBLICATIONS

Bundgaard, Design of Produrgs, 1985, Chapter 1, p. 1-4.*
'Analogue', http://www.merriam-webster.com/dictionary/analog?show=1&t=1318960382, accessed Oct. 17, 2011.*
Carbapenemase-producing Enterobacteriaceae (CPE), https://www.publichealthontario.ca/en/eRepository/RPAP_Annex_A_CPE_Information_Sheet_2013.pdf, retrieved Nov. 1, 2016.*
Arnold et al, 2011, South Med J, vol. 104(1), p. 40-45.*
Pitout, Carbapenemase-producing Klebsiella pneumoniae, a Key Pathogen Set for Global Nosocimial Dominance, Antimicrobial Agents and Chemotherapy, vol. 59, No. 10, p. 5873-5884. (Year: 2015).*
O'Neil et al., The Merck Index: An Encyclopedia of Chemicals, Drugs, and Biologicals, Merck & Co., NJ, 14th Ed., 2006: pp. 1560-1561. No. 0009083.
G. H. Talbot, "b-Lactam antimicrobials: what have you done for me lately?", Ann. N. Y. Acad. Sci., 1277 (2013) 76-83.
Watkins, et al., "Novel β-lactamase inhibitors: a therapeutic hope against the scourge of multidrug resistance", Frontiers in Microbiology—Antimicrobials, Resistance and Chemotherapy, Dec. 24, 2013, vol. 4, Article 392, pp. 1-8.
"Imipenem." The Merck Index: An Encyclopedia of Chemicals, Drugs, and Biologicals: Edition, 2013, p. 914, Whitehouse Station, NJ.
Antimicrobial Resistance Surveillance in Europe 2015 from the European Centre for Disease Prevention and Control, Stockholm, ECDC, 2017. www.ecdc.europa.eu.
Bebrone et al., "CENTA as a Chromogenic Substrate for Studying β-Lactamases," Antimicrobial Agents and Chemotherapy (Jun. 2001), Mar. 2, 2001, vol. 45 (6), pp. 1868-1871.

(Continued)

*Primary Examiner* — Rebecca L Anderson
*Assistant Examiner* — Karen Cheng
(74) *Attorney, Agent, or Firm* — Foley & Lardner LLP

(57) ABSTRACT

Described herein are compounds and their use in the treatment of infections. The compound of formula (I), their derivatives, analogs, tautomeric forms, stereoisomers, polymorphs, solvates, pharmaceutically acceptable salts and pharmaceutical compositions described herein are also useful as β-lactamase inhibitors, which restore or enhance the antibiotic spectrum of a suitable antibiotic agent. The compounds of formula (I) act as inhibitors of β-lactamases. These compounds restore/potentiate the activities of β-lactam antibiotics against carbapenemases. These compounds find use in diagnostic method for detecting β-lactamases.

Formula (I)

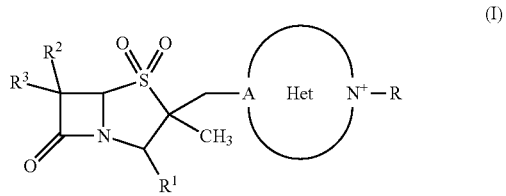

19 Claims, 1 Drawing Sheet

(56) References Cited

OTHER PUBLICATIONS

Drawz et al., "Three Decades of β-Lactamase Inhibitors," Clinical Microbiology Reviews, Jan. 2010, vol. 23(1), pp. 160-201.
Examination Report for Philippine Patent Application No. 1/2013/501042, dated Mar. 17, 2017.
FDA Center for Drug Evaluation and Research, Application No. 206829Orig1s000, Cross Discipline Team Leader Review, 2014 (34 pages).
Fluckiger et al., "Integration of Pharmacokinetics and Pharmacodynamics of Imipenem in a Human-Adapted Mouse Model," Antimicrobial Agents and Chemotherapy (Sep. 1991), Jul. 5, 1991, vol. 35 (9), pp. 1905-1910.
Gupta et al., "Carbapenem-Resistant Enterobacteriaceae: Epidemiology and Prevention," Clinical Infectious Diseases, Jul. 1, 2011, vol. 53 (1), pp. 60-67.
Jamieson et al., "In Vitro and In Vivo Activities of AM-112, a Novel Oxapenem," Antimicrobial Agents and Chemotherapy (May 2003), Feb. 4, 2003, vol. 47 (5), pp. 1652-1657.
Papadimitriou-Olivgeris et al., "Performance of chromID® CARBA medium for carbapenemases-producing enterobacteriaceae detection during rectal screening," The European Journal of Clinical Microbiology & Infectious Diseases (2014), Aug. 4, 2013, vol. 33, pp. 35-40.
Queenan et al., "Carbapenemases: the Versatile β-Lactamases," Clinical Microbiology Reviews, Jul. 2007, vol. 20 (3), pp. 440-458.
Sader et al., "Ceftazidime/avibactam tested against Gram-negative bacteria from intensive care unit (ICU) and non-ICU patients, including those with ventilator-associated pneumonia," International Journal of Antimicrobial Agents, 2015, vol. 46, pp. 53-59.
Tsakris et al., "Spread of low-level carbapenem-resistant Acinetobacter baumannii clones in a tertiary care Greek hospital," Journal of Antimicrobial Chemotherapy, Oct. 29, 2003, vol. 52 (6), pp. 1046-1047.
Vrioni et al., "Comparative Evaluation of a Prototype Chromogenic Medium (ChromID CARBA) for Detecting Carbapenemase-Producing Enterobacteriaceae in Surveillance Rectal Swabs," Journal of Clinical Microbiology, Jun. 2012, vol. 50 (6), pp. 1841-1846.
Examination Report for Chilean Patent Application No. 2013-001482, dated Dec. 16, 2015.
Reed, L.J. et al.,"Simple Method for Estimating Fifty Percent Endpoints," The American Journal of Hygiene, May 1938, vol. 27, pp. 493-497.
Wyeth, Chilean Unpublished Appl. Ser. No. 0848-2003 entitled "Bicyclic 6-Alkylidene-Penems as β-Lactamases Inhibitors", dated Apr. 28, 2003 (286 pages).
Wyeth, Chilean Unpublished Appl. Ser. No. 0852-2003 entitled "Tricyclic 6-Alkylidene-Penems as β-Lactamases Inhibitors", dated Apr. 28, 2003 (288 pages).

* cited by examiner

Double Disk Synergy Test for detection of KPC β-lactamases
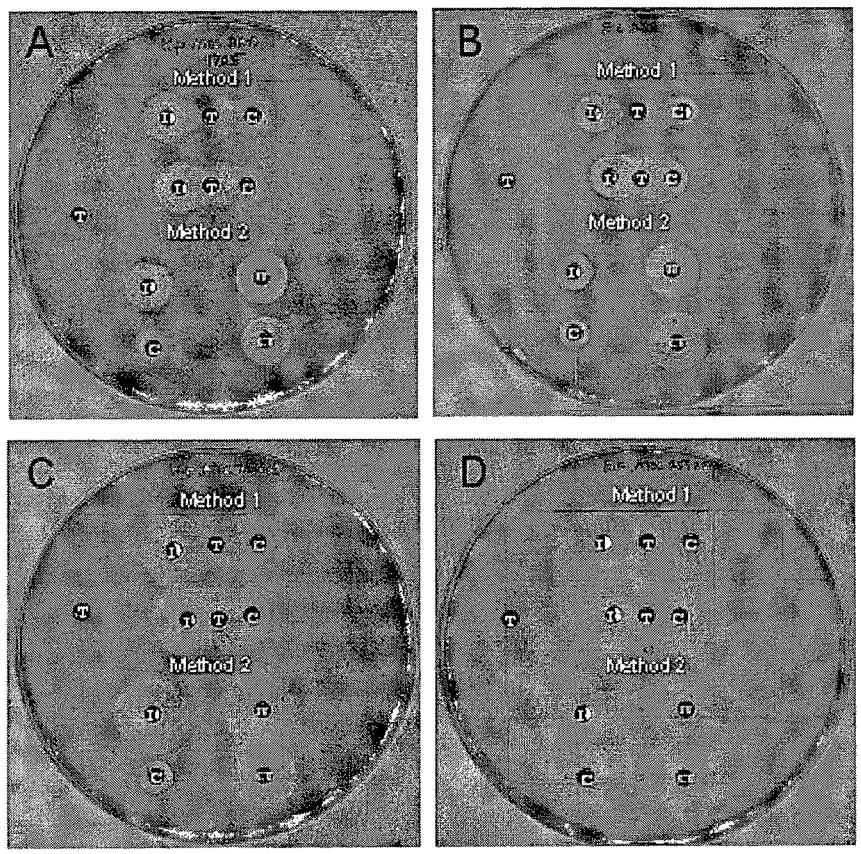
Double disk synergy test of Compound-1 against (A) *K. pneumoniae* ATCC BAA 1705 [KPC2 producer], (B) *E.coli* 233 [KPC3 producer], (C) *K. pneumoniae* ATCC 700603 [SHV18 producer], (D) *E. coli* ATCC 25922.
I = Imipenem; C= Ceftazidime; T= Compound-1; IT = Imipenem + Compound-1; CT = Ceftazidime + Compound-1.

COMPOUNDS AND THEIR USE

FIELD

Described herein are the use of β-lactam compounds as β-lactamase inhibitor, their analogs, derivatives, tautomeric forms, stereoisomers, polymorphs, solvates, pharmaceutically acceptable salts, esters, prodrugs and metabolites thereof, for treating bacterial infections in combination with suitable antibiotic. The pharmaceutical compositions of these compounds for treating bacterial infections are described. The compounds described herein are used as diagnostic reagent for the detection of β-lactamases.

BACKGROUND

The β-lactam type antibiotics, namely penicillins, cephalosporins, carbapenems, monobactams are frequently used antibiotics. It is known that β-lactamases produced by microorganisms hydrolyze the β-lactam ring thereby deactivating antibiotic activity. In order to inhibit the β-lactamases, β-lactamase inhibitors are administered in combination with antibiotics. These inhibitors function by binding to the β-lactamase enzymes more efficiently than the β-lactam antibiotic itself. This combination helps the antibiotic to exert its antibiotic effect without being degraded by the β-lactamase enzymes. Several antibiotic/β-lactamase inhibitor combinations exist in the market for example, Ampicillin/Sulbactam, Amoxicillin/Clavulanate, Ticarcillin/Clavulanate, Piperacillin/Tazobactam, etc. These β-lactam/β-lactamase inhibitor combination antibiotics are being used for the treatment of infections caused by bacteria producing β-lactamases excepting especially carbapenemases and inhibitor-resistant β-lactamases in the community and in the hospital setting.

A growing problem by the widespread use of antimicrobials especially β-lactam antibiotics is in the development of antimicrobial resistance. A major cause for antibiotic resistance is due to β-lactamases (e.g., carbapenemases, cephalosporinases, penicillinases, ESBLs, inhibitor-resistant β-lactamases, etc). Among many known β-lactamases, Carbapenemases (e.g., KPC, Sme, NMC-A, IMI, etc.) are recently identified, which are capable of hydrolyzing all classes of β-lactam antibiotics (Drawz, S. M. and Bonomo, R. A. *Clin. Microbiol. Rev.* 2010, 23(1), 160-201). These enzymes are known for their role in multidrug resistance (MDR). In view of the pressing need in the development of effective β-lactamase inhibitor (BLI) against the evolving β-lactamases, our research efforts in identifying potential BLIs resulted in the compound of formula (I).

To address the need for proper diagnostic method for specific detection of β-lactamases, diagnostic method was identified using the compounds of formula (I).

Among many β-lactamase inhibitors that are known in the literature, compounds of formula (A) are disclosed in U.S. Pat. No. 4,562,073,

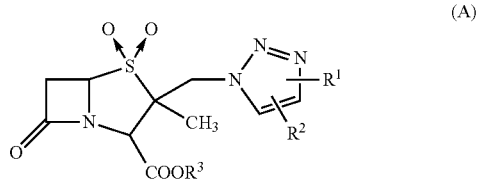

(A)

wherein $R^1$ is hydrogen or trialkylsilyl; $R^2$ is hydrogen, trialkylsilyl or $COOR_2'$ wherein $R_2'$ is hydrogen, $C_{1-18}$ alkyl, $C_{2-7}$ alkoxymethyl, $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl, alkoxycarbonylmethyl, $C_{4-9}$ alkoxycarbonylethyl, phthalidyl, crotonolacton-4-yl, gamma-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1,3-dioxoden-4-yl)methyl, $C_{8-13}$ benzoyloxyalkyl or group for forming a pharmaceutically acceptable salt; and $R^3$ has the same meaning as above $R_2'$.

Our U.S. Pat. No. 7,687,488 B2 (Indian equivalent IN 1217CHE2006) disclosed compounds of the formula (B). These compounds were shown to potentiate the activity of antibiotics.

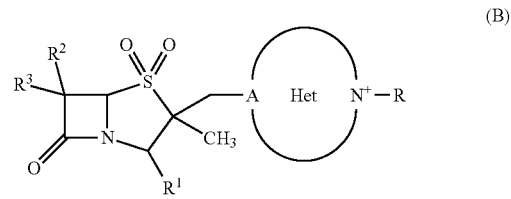

(B)

wherein A=C or N; Het is a three- to seven-membered heterocyclic ring; $R^1$ represents carboxylate anion or —$COOR^4$ wherein $R^4$ represents hydrogen, carboxylic acid protecting group or a pharmaceutically acceptable salt; $R^2$ and $R^3$ may be same or different and independently represent hydrogen, halogen, amino, protected amino or optionally substituted alkyl, alkenyl, alkynyl and the like; R is represented by substituted or unsubstituted alkyl, alkenyl, aryl, aralkyl, cycloalkyl, oxo, heterocyclyl, heterocyclylalkyl groups.

There is a widespread need for β-lactamase inhibitors which are capable of inhibiting the β-lactamase enzymes, in particular, carbapenemases producing multidrug resistant bacteria. Moreover, there is a unmet medical need for combination drugs in antibiotics, specifically β-lactam antibiotics and β-lactamase inhibitors which overcome the bacterial resistance.

Objectives

One objective herein is to use the β-lactam compounds of the formula (I) as β-lactamase inhibitor in combination with suitable antibiotics for treating infection caused by bacteria producing β-lactamases like carbapenemases, cephalosporinases, penicillinases, ESBLs, inhibitor-resistant β-lactamases, ESBLs and the like.

Another objective herein is to provide a pharmaceutical composition with the compounds of formula (I) in combination with suitable antibiotics.

Yet another objective herein is to provide a method of treating or preventing bacterial infection in a host, typically an animal and most typically a human, including administering to the host a therapeutic amount of compound of formula (I) or a pharmaceutically acceptable salt and/or prodrug therein along with β-lactam antibiotics.

Another objective herein is to provide a diagnostic reagent for the detection of β-lactamases. The said β-lactamases belong to the families of KPC (e.g., KPC-2, KPC-3) & ESBL (e.g., SHV18) producing Enterobacteriaceae.

One more objective herein is to restore/potentiate the activity of antibiotics especially β-lactam antibiotics such as Penicillins, Cephalosporins, Carbacephem, Oxacephem, Carbapenems, Penams, Cephamycins, Penems and Monobactams towards carbapenemases and ESBLs by combining with compound of formula (I).

It is therefore an object of the present invention to provide a compound for inhibiting β-lactamase; and/or a pharmaceutical composition comprising said compound; and/or an improved method for inhibiting β-lactamase in a cell; and/or an improved method for the treatment and/or prevention of a condition mediated by β-lactamase; and/or an improved method for the treatment and/or prevention of a bacterial infection along with β-lactam antibiotic; and/or to restore/potentiate the activity of antibiotics; or at least to provide the public with a useful choice.

SUMMARY

Described herein is a method or use of compound of formula (I), their derivatives, analogs, tautomeric forms, stereoisomers, polymorphs, solvates, pharmaceutically acceptable compositions, metabolites, prodrugs, pharmaceutically acceptable salts and esters thereof;

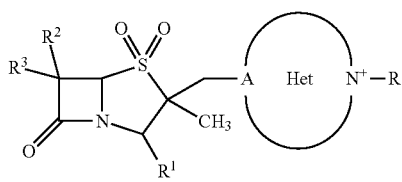

(I)

In particular, provided herein are compound of formula (I), their derivatives, analogs, tautomeric forms, stereoisomers, polymorphs, solvates, metabolites, prodrugs, hydrates, pharmaceutically acceptable salts and esters, for use in the inhibition of β-lactamases comprising carbapenemases, cephalosporinases, penicillinases, ESBLs, inhibitor-resistant β-lactamases, produced by bacteria; potentiating/restoring the activity of antibiotics, comprising administering a therapeutically effective amount of compound of formula (I), to a subject in need thereof;
wherein
A=C or N;
Het represents substituted or unsubstituted three- to seven-membered heterocyclic ring;
$R^1$ represents carboxylate anion or —COOR$^4$; wherein $R^4$ represents hydrogen, $C_1$-$C_6$alkyl, $C_6$-$C_{10}$aryl, $C_6$-$C_{10}$aryl$C_1$-$C_6$alkyl methoxybenzyl, nitrobenzyl, silyl, diphenylmethyl, proxetil, axetil, cilexetil, pivoxil, hexetil, daloxate or a pharmaceutically acceptable salt; $R^2$ and $R^3$ may be same or different and independently represent hydrogen, halogen, amino, protected amino selected from the group consisting of tritylamino, acylamino such as phenylacetylamino, phenoxyacetylamino and benzoylamino or optionally substituted $C_1$-$C_6$alkyl, $C_2$-$C_6$alkenyl and $C_2$-$C_6$alkynyl;
R represents substituted or unsubstituted $C_1$-$C_6$alkyl, $C_2$-$C_6$alkenyl, $C_6$-$C_{10}$aryl, $C_6$-$C_{10}$aryl$C_1$-$C_6$alkyl, $C_3$-$C_{12}$cycloalkyl, oxo, heterocyclyl and heterocyclylalkyl groups. when the groups R, $R^2$ and $R^3$ are substituted, the substituents which may be one or more are selected from lower alkyl ($C_1$-$C_4$alkyl such as methyl, ethyl, propyl and isopropyl); lower alkoxy ($C_1$-$C_4$alkoxy such as methoxy, ethoxy and propoxy); lower alkylthio ($C_1$-$C_4$alkylthio such as methylthio and ethylthio); lower alkylamino ($C_1$-$C_4$alkylamino such as methylamino, ethylamino and propylamino); cyclo(lower)alkyl ($C_5$-$C_6$cycloalkyl such as cyclopentyl and cyclohexyl); cyclo(lower)alkenyl ($C_5$-$C_6$cycloalkenyl such as cyclohexenyl and cyclohexadienyl); hydroxy; halogen (chloro, bromo, fluoro and iodo); amino; protected amino; cyano; nitro; carbamoyl; —CONH $C_1$-$C_4$alkyl-COO—$C_1$-$C_4$alkyl; carboxy; protected carboxy; —COO—$C_1$-$C_4$alkyl; —CO-heterocyclyl; sulfonyl; sulfamoyl; imino; oxo; amino(lower)alkyl such as aminomethyl, aminoethyl and aminopropyl; halo(lower)alkyl such as trifluoromethyl (—$CF_3$), fluoromethyl, fluoroethyl, bromomethyl and difluoromethyl; carboxylic acid and carboxylic acid derivatives such as hydroxamic acid, ester and amide. Preferred substituents are $C_1$-$C_4$alkyl, $C_1$-$C_4$alkoxy, $C_1$-$C_4$alkylthio, $C_1$-$C_4$alkylamino, hydroxyl, halogen and trihalomethyl. The substituents are further optionally substituted with $C_1$-$C_4$alkoxycarbonyl$C_1$-$C_4$alkyl, hydroxy$C_1$-$C_4$alkyl; $C_1$-$C_4$alkyl, $C_6$-$C_{10}$aryl, heterocyclyl and esters.

In one aspect, provided herein are compound of formula (II), their derivatives, analogs, tautomeric forms, stereoisomers, polymorphs, solvates, metabolites, prodrugs, hydrates, pharmaceutically acceptable salts and esters for use in inhibition of carbapenemases produced by bacteria; potentiating/restoring the activity of antibiotics, comprising administering a therapeutically effective amount of compound of formula (II), to a subject in need thereof;

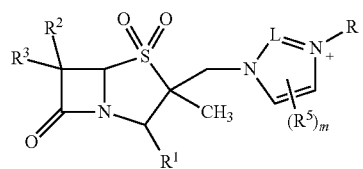

(II)

wherein
L=C or N;
R, $R^1$, $R^2$ and $R^3$ are as defined earlier.
$R^5$ represents hydrogen, $C_1$-$C_6$alkyl, $C_1$-$C_6$alkoxy, $C_1$-$C_6$alkylthio, $C_1$-$C_6$alkylamino, hydroxyl, halogen and trihalomethyl; and
m is 0, 1 or 2.

In another aspect, provided herein is compound for use in treating and/or preventing infections caused by carbapenemase producing bacteria, comprising administering therapeutically effective amount of compound of formula (I), to a subject in need thereof.

In yet another aspect, provided herein is compound for use in treating and/or preventing infection caused by carbapenemase producing bacteria comprising administering therapeutically effective amount of compound of formula (I), in combination with suitable antibiotics to a subject in need thereof.

In yet other aspect, provided herein is the compound for use, for treating infections caused by β-lactamases expressed by gram negative bacteria.

In yet other aspect, provided herein is the compound for use, wherein bacteria are selected from *Klebsiella pneumoniae* and *E. coli*.

In yet other aspect, provided herein is the compound for use, wherein the carbapenemases are selected from KPC-2 and KPC-3.

In yet another aspect, provided herein is the method of treatment or prevention of infection caused by carbapenemase producing bacteria comprising administering therapeutically effective amount of compound of formula (I).

Another aspect herein includes detection of β-lactamases expressed by Enterobacteriaceae and non-Enterobacteriaceae.

Yet another aspect herein includes use of compound of formula (I) as a diagnostic reagent for the detection of β-lactamases. The said β-lactamases belong to families of KPC-2, KPC-3 and also ESBLs such as SHV18 producing Enterobacteriaceae.

In one embodiment, provided herein is pharmaceutical composition, comprising a compound of formula (I), as an active ingredient to treat or prevent infections caused by carbapenemase producing bacteria.

In another embodiment, provided herein is pharmaceutical composition comprising a compound of formula (I), as an active ingredient to treat or prevent infections caused by carbapenemase producing bacteria along with
  a. one or more compounds of formula (I);
  b. one or more antibiotics and
  c. one or more pharmaceutically acceptable carrier.

In yet another embodiment, the antibiotics are selected from β-lactam antibiotics.

In yet other embodiment, provided herein are the compounds, (2S,3S,5R)-3-Methyl-3-(3-methyl-imidazol-3-ium-1-ylmethyl)-4,4,7-trioxo-4-thia-1-azabicyclo[3.2.0]heptane-2-carboxylate and (2S,3S,5R)-3-Methyl-3-(4-methyl-3-methyl-imidazol-3-ium-1-ylmethyl)-4,4,7-trioxo-4-thia-1-aza-bicyclo[3.2.0]heptane-2-carboxylate, their derivatives, analogs, tautomeric forms, stereoisomers, polymorphs, solvates, metabolites, prodrugs, pharmaceutically acceptable salts and esters.

In yet another aspect the compounds (2S,3S,5R)-3-Methyl-3-(3-methyl-imidazol-3-ium-1-ylmethyl)-4,4,7-trioxo-4-thia-1-azabicyclo[3.2.0]heptane-2-carboxylate; (2S,3S,5R)-3-Methyl-3-(4-methyl-3-methyl-imidazol-3-ium-1-ylmethyl)-4,4,7-trioxo-4-thia-1-aza-bicyclo[3.2.0]heptane-2-carboxylate and their derivatives, analogs, tautomeric forms, stereoisomers, polymorphs, solvates, metabolites, prodrugs, pharmaceutically acceptable salts and esters for use in the inhibition of β-lactamases, without limitation, carbapenemases, cephalosporinases, penicillinases, ESBLs and inhibitor-resistant β-lactamases.

In yet other aspects, described herein are the compound of formula (I) for use in the treatment and/or prevention of bacterial resistance to an antibiotic.

BRIEF DESCRIPTION OF FIGURES

FIG. 1: Double Disk Synergy Test for detection of KPC β-lactamases

DETAILED DESCRIPTION

β-Lactam compounds of formula (I),

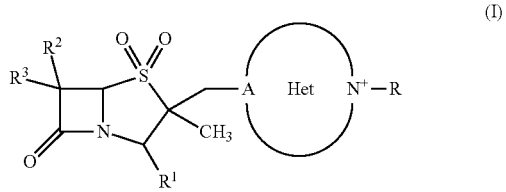

(I)

their derivatives, analogs, tautomeric forms, stereoisomers, polymorphs, solvates, their pharmaceutically acceptable compositions, pharmaceutically acceptable salts and esters thereof, for use in the inhibition of carbapenemases produced by bacteria; potentiating/restoring the activity of antibiotics, wherein:

Het is a three to seven membered heterocyclic ring which may have suitable substituent(s) and, preferable heterocyclic group such as pyrrolyl, pyrrolinyl, imidazolyl, pyrazolyl, pyridyl, pyrimidinyl, pyrazinyl, piperidinyl, furanyl, thiophenyl, pyrrolidinyl, piperazinyl, oxazolidinyl, thiazolyl, pyridazinyl, tetrazolyl (e.g. 1H-tetrazolyl, 2H-tetrazolyl, etc.), imidazolidinyl, triazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl and 1,2,5-thiadiazolyl.

The defined heterocyclic groups may optionally be substituted with one or more substituents, suitable substituent(s) such as: lower alkyl ($C_1$-$C_4$ alkyl such as methyl, ethyl and propyl); lower alkoxy ($C_1$-$C_4$ alkoxy such as methoxy, ethoxy and propoxy); lower alkylthio ($C_1$-$C_4$ alkylthio such as methylthio and ethylthio); lower alkylamino ($C_1$-$C_4$ alkylamino such as methylamino, ethylamino and propylamino); cyclo(lower)alkyl ($C_5$-$C_6$ cycloalkyl such as cyclopentyl and cyclohexyl); cyclo(lower)alkenyl ($C_5$-$C_6$ cycloalkenyl such as cyclohexenyl and cyclohexadienyl); hydroxyl; halogen (chloro, bromo, fluoro and iodo); amino; protected amino; cyano; nitro; carboxy; protected carboxy; sulfamoyl; imino; oxo; amino(lower)alkyl (aminomethyl, aminoethyl and aminopropyl); halogen and trihalomethyl ($-CF_3$). Preferred substituents are $C_1$-$C_4$ alkyl, $C_1$-$C_4$ alkoxy, $C_1$-$C_4$ alkylthio, $C_1$-$C_4$ alkylamino, hydroxyl, halogen and trihalomethyl. The substituents are further optionally substituted.

Typically, the moiety Het is unsubstituted or carries one or more substituents as defined above.

Preferably Het represents a five- to six-membered heterocyclic ring comprising one or two heteroatoms, including the quaternized nitrogen. More preferably, Het is selected from pyrrolyl, pyrrolinyl, imidazolyl, triazolyl, pyrazolyl, pyridyl, pyrimidinyl, pyrazinyl, piperidinyl, furanyl, thiophenyl, pyrrolidinyl, piperazinyl, oxazolidinyl, thiazolyl, pyridazinyl, pyrrolidinyl and imidazolidinyl.

Preferably, Het is an aromatic ring.

More preferably, Het represents five membered heterocyclic ring;

$R^1$ represents carboxylate anion or $-COOR^4$ wherein $R^4$ represents hydrogen, $-C_6$alkyl, $C_6$-$C_{10}$aryl, $C_6$-$C_{10}$aryl$C_1$-$C_6$alkyl, methoxybenzyl, nitrobenzyl, silyl, diphenylmethyl, proxetil, axetil, cilexetil, pivoxil, hexetil, daloxate or a pharmaceutically acceptable salt;

$R^2$ and $R^3$ independently represent hydrogen, halogen, amino, protected amino such as tritylamino, acylamino such as phenylacetylamino, phenoxyacetylamino and benzoylamino; optionally substituted alkyl, alkenyl or alkynyl;

Preferably R is selected from $-(CH_2)_n-CH_3$, $-(CH_2)_nC_6H_5$, $-(CH_2)_n-CH=CH_2$, $-CH_2-CONH_2$, $-CH_2-COO-(C_1-C_4\text{alkyl})$ comprising $-CH_2COOBu^t$, $-(CH_2)_n$CO-heterocyclyl, $-CH_2-CONH-(CH_2)_n-COOEt$, where n is an integer ranging from 0 to 5.

More preferably, R is $-(CH_2)_n-CH_3$, $-(CH_2)_nC_6H_5$, $-(CH_2)_n-CH=CH_2$, $-CH_2-CONH_2$ or $-CH_2COOBu^t$.

As used herein, a $C_1$-$C_6$alkyl group or moiety is a linear or branched alkyl group or moiety containing from 1 to 6 carbon atoms. Typically a $C_1$-$C_6$ alkyl group or moiety is a $C_1$-$C_4$ alkyl group or moiety. A $C_1$-$C_4$ alkyl group or moiety is a linear or to branched alkyl group or moiety containing from 1 to 4 carbon atoms. Examples of $C_1$-$C_6$ alkyl groups and moieties include, without limitation, methyl, ethyl, n-propyl, propyl, n-butyl, i-butyl, t-butyl, 3-methyl-butyl, pentyl and hexyl. Examples of $C_1$-$C_4$ alkyl groups and moieties include, without limitation, methyl, ethyl, n-propyl, i-propyl, n-butyl, i-butyl and t-butyl. For the avoidance of doubt, where two alkyl moieties are present in a group, the alkyl moieties may be the same or different, which may be optionally substituted by one or more substituents.

The term "$C_2$-$C_6$alkenyl" refers to an aliphatic hydrocarbon group containing a carbon-carbon double bond and which may be straight or branched chain having about 2 to 6 carbon atoms, which may be optionally substituted by one or more substituents. Preferred alkenyl groups include, without limitation, ethenyl, 1-propenyl, 2-propenyl, isopropenyl, 2-methyl-1-propenyl, 1-butenyl and 2-butenyl.

As used herein, a $C_6$-$C_{10}$aryl group or moiety is typically phenyl or naphthyl. Phenyl is preferred.

The term "$C_6$-$C_{10}$aryl$C_1$-$C_6$alkyl" refers to an aryl group directly bonded to an alkyl group, which may be optionally substituted by one or more substituents.

Preferred arylalkyl groups include, without limitation, —$CH_2C_6H_5$, —$C_2H_4C_6H_5$, —$CH(CH_3)C_6H_5$ and the like.

As used herein, the term "heterocyclyl" refers to a 5 to 10 membered heterocyclyl group or moiety is a monocyclic non-aromatic, saturated or unsaturated $C_5$-$C_{10}$ carbocyclic ring in which one or more, for example 1, 2, 3 or 4 of the carbon atoms are replaced with hetero atoms selected from N, O, S, S(O) and S(O)$_2$. Typically, it is a 5 to 6 membered ring. Suitable heterocyclyl groups and moieties include pyrazolidinyl, piperidinyl, piperazinyl, thiomorpholinyl, S-oxo-thiomorpholinyl, S,S-dioxo-thiomorpholinyl, morpholinyl, pyrrolidinyl, pyrrolinyl, imidazolidinyl, imidazolinyl, 1,3-dioxolanyl, 1,4-dioxolyl and pyrazolinyl groups and moieties. Pyrazolidinyl, piperidyl, piperazinyl, pyrazolidinyl, morpholinyl and imidazolidinyl groups and moieties are preferred.

The term "heterocyclylalkyl" refers to heterocyclyl group directly bonded to an alkyl group, which may be substituted or unsubstituted.

The term "$C_3$-$C_{12}$cycloalkyl" refers to non-aromatic mono or polycyclic ring system of about 3 to 12 carbon atoms, which may be optionally substituted by one or more substituents. Preferred cycloalkyl groups include, without limitation, cyclopropyl, cyclobutyl, cyclopentyl, cyclohexyl, cyclooctyl and perhydronaphthyl.

The term "analog" includes a compound, which differs from the parent structure by one or more C, N, O or S atoms. Hence, a compound in which one of the N atoms in the parent structure is replaced by an S atom is an analog of the former.

The term "derivative" refers to a compound obtained from a compound according to formula (I), an analog, tautomeric form, stereoisomer, polymorph, hydrate, pharmaceutically acceptable salt or pharmaceutically acceptable solvate thereof, by a simple chemical process converting one or more functional groups, such as, by oxidation, hydrogenation, alkylation, esterification, halogenation and the like.

The term "stereoisomer" includes isomers that differ from one another in the way the atoms are arranged in space, but whose chemical formulae and structures are otherwise identical. Stereoisomers include enantiomers and diastereoisomers.

The term "tautomers" include readily interconvertible isomeric forms of a compound in equilibrium. The keto-enol tautomerism is an example.

The term "polymorphs" include crystallographically distinct forms of compounds with chemically identical structures.

The term "pharmaceutically acceptable solvates" includes combinations of solvent molecules with molecules or ions of the solute compound.

Representative compounds (1-13) exhibiting β-lactamase inhibitory properties include but not limited to:

1. 1-{[(2S,3S,5R)-2-Carboxy-3-methyl-4,4,7-trioxo-4-thia-1-azabicyclo[3.2.0]hept-3-yl]methyl}-3-methyl-1H-1,2,3-triazol-3-ium;
2. 1-{[(2S,3S,5R)-2-Carboxy-3-methyl-4,4,7-trioxo-4-thia-1-azabicyclo[3.2.0]hept-3-yl]methyl}-3-ethyl-1H-1,2,3-triazol-3-ium;
3. 1-{[(2S,3S,5R)-2-Carboxy-3-methyl-4,4,7-trioxo-4-thia-1-azabicyclo[3.2.0]hept-3-yl]methyl}-3-n-propyl-1H-1,2,3-triazol-3-ium;
4. 1-{[(2S,3S,5R)-2-Carboxy-3-methyl-4,4,7-trioxo-4-thia-1-azabicyclo[3.2.0]hept-3-yl]methyl}-3-allyl-1H-1,2,3-triazol-3-ium;
5. 1-{[(2S,3S,5R)-2-Carboxy-3-methyl-4,4,7-trioxo-4-thia-1-azabicyclo[3.2.0]hept-3-yl]methyl}-3-(2-amino-2-oxoethyl)-1H-1,2,3-triazol-3-ium and the corresponding acid;
6. 1-{[(2S,3S,5R)-2-Carboxy-3-methyl-4,4,7-trioxo-4-thia-1-azabicyclo[3.2.0]hept-3-yl]methyl}-3-(2-t-butoxy-2-oxoethyl)-1H-1,2,3-triazol-3-ium and the corresponding acid;
7. 1-{[(2S,3S,5R)-2-Carboxy-3-methyl-4,4,7-trioxo-4-thia-1-azabicyclo[3.2.0]hept-3-yl]methyl}-3-(2-morpholin-4-yl-2-oxoethyl)-1H-1,2,3-triazol-3-ium and the corresponding acid;
8. 1-{[(2S,3S,5R)-2-Carboxy-3-methyl-4,4,7-trioxo-4-thia-1-azabicyclo[3.2.0]hept-3-yl]methyl}-3-{2[(2-ethoxy-2-oxoethyl)amino]-2-oxoethyl}-1H-1,2,3-triazol-3-ium and the corresponding acid;
9. 1-{[(2S,3S,5R)-2-Carboxy-3-methyl-4,4,7-trioxo-4-thia-1-azabicyclo[3.2.0]hept-3-yl]methyl}-3-{2-[(3-ethoxy-3-oxopropyl)amino]-2-oxoethyl}-1H-1,2,3-triazol-3-ium and the corresponding acid;
10. 1-{[2S,3S,5R)-2-Carboxy-3-methyl-4,4,7-trioxo-4-thia-1-azabicyclo[3.2.0]hept-3-yl]methyl}-3-(2-{[1-(ethoxycarbonyl)-2-hydroxypropyl]amino}-2-oxoethyl)-1H-1,2,3-triazol-3-ium and the corresponding acid;
11. 1-{[(2S,3S,5R)-2-Carboxy-3-methyl-4,4,7-trioxo-4-thia-1-azabicyclo[3.2.0]hept-3-yl]methyl}-3-benzyl-1H-1,2,3-triazol-3-ium and the corresponding acid;
12. (2S,3S,5R)-3-Methyl-3-(3-methyl-imidazol-3-ium-1-yl-methyl)-4,4,7-trioxo-4-thia-1-azabicyclo[3.2.0]heptane-2-carboxylate and the corresponding acid; and
13. (2S,3S,5R)-3-Methyl-3-(4-methyl-3-methyl-imidazol-3-ium-1-ylmethyl)-4,4,7-trioxo-4-thia-1-aza-bicyclo[3.2.0]heptane-2-carboxylate and the corresponding acid.

These compounds (1 to 11) were prepared by following the procedures provided in U.S. Pat. No. 7,687,488 (Indian equivalent IN 1217CHE2006).

The compounds 12 and 13 are prepared according to reaction scheme as shown below:

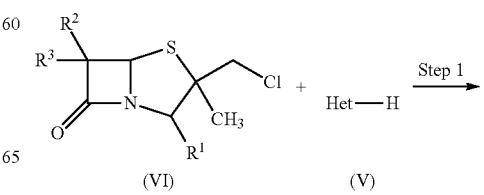

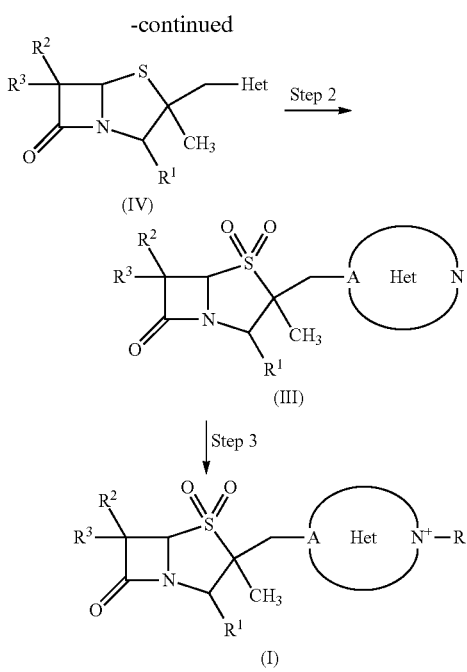

wherein Het is

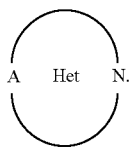

Compound of formula (IV) was obtained by the reaction of compound of formula (VI) with the compound of formula (V) in Step-1. In Step-2, the compound of formula (IV) was converted to the compound of formula (III). The conversion of compound of formula (III) to a compound of formula (I) may be carried out using silylating agent selected from hexamethyldisilazane (HMDS), trimethylchlorosilane (TMCS), trimethylsilyl iodide (TMSI), N,O-bis-(trimethylsilyl)-acetamide (BSA), methyltrimethylsilyltrifluoroacetamide (MSTFA), N,O-bis(trimethylsilyl)trifluoroacetamide (BSTFA), methyldichlorosilane, dimethyldichlorosilane, diphenyldichlorosilane, N-methylsilylacetamide (MSA), bistrimethylsilylurea and the like in the presence of solvents like acetone, methanol, tetrahydrofuran, chloroform, dichloromethane, dichloroethane, ethyl acetate, N,N-dimethylformamide (DMF), Dimethylacetamide (DMAc) and the like or a mixture thereof. The compound of formula (I) was obtained by the reaction of compound of formula (III) with a suitable R—X (X=halogen).

The β-lactam compounds described herein are preferably formed as inner salts. When the representative substitution on R is carboxylic acid or amino group, it may be further converted to pharmaceutically acceptable salts. Bases used for making salts of carboxylic acid groups are selected from base such as sodium hydroxide, sodium methoxide, sodium bicarbonate, sodium carbonate, potassium bicarbonate, potassium carbonate, calcium hydroxide, magnesium hydroxide and the like, in solvents like ether, tetrahydrofuran, methanol, t-butanol, dioxane, isopropanol, ethanol, etc. Mixture of solvents may be used. Acid addition salts could also be prepared using appropriate acid.

The stereoisomers of the compounds forming part of this invention may be prepared by using reactants in their single enantiomeric form, in the process wherever possible or by conducting the reaction in the presence of reagents or catalysts in their single enantiomeric form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like, wherever applicable or by using chiral bases such as brucine, cinchona alkaloids, their derivatives and the like.

Prodrugs of the compounds of formula (I) are also contemplated by this invention. A prodrug is an active or inactive compound that is modified chemically through in-vivo physiological action, such as hydrolysis, metabolism and the like, into a compound of this invention following administration of the prodrug to a patient. The suitability and techniques involved in making, using prodrugs are well known by those skilled in the art.

Various polymorphs of compound of general formula (I) may be prepared by crystallization of compound of formula (I) under different conditions known in the prior art. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by Solid Probe NMR Spectroscopy, IR Spectroscopy, Differential Scanning calorimetry, Powder X-ray Diffraction or such other techniques.

Pharmaceutically acceptable solvates of the compounds of formula (I) may be prepared by conventional methods such as dissolving the compounds of formula (I) in solvents such as water, methanol, ethanol, mixture of solvents such as acetone:water, dioxane:water, N,N-dimethylformamide:water and the like, preferably water and recrystallizing by using different crystallization techniques.

It should be noted that compounds described herein may contain groups that may exist in tautomeric forms and though one form is named, described, displayed and/or claimed herein, all the forms are intended to be inherently included in such name, description, display and/or claim.

The β-lactam compounds disclosed herein in combination with a β-lactam antibiotic are useful for the treatment of microbial infections in humans and other warm blooded animals, under both parenteral, topical and/or oral administration. In addition to the compounds of formula (I), the pharmaceutical compositions may also contain or be co-administered with one or more known drugs selected from other clinically useful antibiotic agents such as Penicillins (Piperacillin, Ticarcillin and the like), Cephalosporins (Ceftazidime, Cefmetazole, Cefotaxime and the like), Penems (Faropenem, Meropenem, Ertapenem and the like), Carbacephem (Loracarbef and the like), Oxacephem (Moxalactam, Latamoxef, Flomoxef and the like), Cephamycins (Cefotetan and the like) Monobactams (Aztreonam, Tigemonam and the like), Aminoglycosides (Streptomycin, Gentamicin, Amikacin and the like), Bacteriocins (Colicins, Microcins and the like), Quinolones (Ciprofloxacin, Moxifloxacin and the like), Sulfonamides (Sulfamethoxazole and the like), Macrolides (Erythromycin, Roxithromycin, Azithromycin and the like), Tetracyclines (Doxycycline, Minocycline and the like), Glycylcyclines (Tigecycline and the like), Oxazolidinones (Linezolid, Torezolid, Radezolid and the like), Lipopeptides (Daptomycin and the like), Polypeptides (Actinomycin, Bacitracin, Colistin, Polymixin B and the like), Polyene antifungals (Natamycin, Nystatin, Amphotericin B and the like), Rifamycins (Rifampicin, Rifabutin, Rifapentine and the like), Chloramphenicol and the like or derivatives thereof.

Antibiotics include Penicillins, Cephalosporins, Carbacephems, Oxacephems, Carbapenems, Penams, Cephamycins, Penems, Monobactams or a combination thereof.

Pencillins include, but are not limited to, Amdinocillin (Mecillinam), Amoxicillin, Ampicillin, Amylpenicillin, Apalcillin, Aspoxicillin, Azidocillin, Azlocillin, Bacampicillin, Carbenicillin, Carindacillin, Clometocillin, Cloxacillin, Cyclacillin (Ciclacillin), Dicloxacillin, Epicillin, Fenbenicillin, Floxacillin (flucloxacillin), Hetacillin, Lenampicillin, Metampicillin, Methicillin, Mezlocillin, Nafcillin, Oxacillin, Penamecillin, Penethecillin, Penicillin G (Procaine Pencillin), Penicillin N, Penicillin O, Penicillin V (Phenoxymethyl Penicillin), Phenethicillin, Piperacillin, Pivampicillin, Propicillin, Quinacillin, Sulbenicillin, Talampicillin, Temocillin, Ticarcillin, Pivmecillinam, Benzathine Penicillin, Benzyl Penicillin, Co-amoxiclav, Lenampicillin or a combination thereof.

Cephalosporins include but not limited to Cephaloridin, Cephradine, Cefoxitin, Cephacetril, Cefoperazone, Cefinenoxime, Cephaloglycin, Cefonicid, Cefodizime, Cefpirome, Cefpiramide, Cefozopran, Cefoselis, Cefluprenam, Cefpimizole, Cefclidin, Cefpodoxime axetil, Cefteram pivoxil, Cefcapene pivoxil, Ceftobiprole, Ceftaroline, Cefquinome, Ceftiofur, Cefovecin, Cefadroxil, Cefalonium, Cefepime, Cefotaxime, Ceftazidime, Cefetamet pivoxil, Cefditoren pivoxil, Cephaloridine, Ceftazidime, Ceftriaxone, Cefbuperazone, Cephalothin, Cephazolin, Cephapirin, Ceftezole, Cefamandole, Cefotiam, Cefotiam hexetil, Cefuroxime, Ceftizoxime, Cefinenoxime, Cefuzonam, Cefsulodin, Cefinetazole, Cefminox, Cephalexin, Cefradine, Cefaclor, Cefadroxil, Cefalonium, Cefprozil, Cefuroxime axetil, Cefixime, Cefpodoxime proxetil, Ceftibuten, Cefdinir, CXA-101(FR264205) or a combination thereof;

Penems include, without limitation, Faropenem and Carbapenems include, without limitation Meropenem, Ertapenem, Doripenem, Biapenem, Panipenem, Ritipenem, Tebipenem, Tomopenem, Sulopenem, Razupenem, Imipenem, ME1036, SM216601 or a combination thereof.

Monobactams include, without limitation, Aztreonam, Carumonam, Tigemonam, BAL19764, BAL30072 or a combination thereof.

β-lactam antibiotics in combination with compounds of the formula (I) may also be co-administered with Aminoglycosides, Bacteriocins, Quinolones, Sulfonamides, Macrolides, Tetracyclines, Glycylcyclines, Oxazolidinones, Lipopeptides, Polypeptides, Rifamycins, Chloramphenicol, Polyene antifungals and derivatives thereof.

Compounds of the formula (I) may also contain or be co-administered with bactericidal/permeability-increasing protein product (BPI) or efflux pump inhibitors to improve activity against gram negative bacteria and bacteria resistant to antimicrobial agents. Antiviral, antiparasitic, antifungal agents and other antibiotics can also be administered in combination with the inhibitor compounds of formula (I). The compound of formula (I) with a suitable antibiotic combination can be used for treating patients with bacterial infections, preoperative patients, postoperative patients, patients in intensive care unit (ICU), patients with nosocomial infections and veterinaries.

The pharmaceutical composition may be in the forms normally employed, such as tablets, capsules, pills, granules, powders, syrups, lozenges, solutions, suspensions, aerosols, transdermal patches, topical creams and ointments and the like, may contain flavoring agents, sweeteners, etc. in suitable solid or liquid carriers or diluents or in suitable sterile media to form injectable solutions or suspensions. The pharmaceutical composition may also contain pharmaceutically acceptable carrier that are known in the prior art.

The compounds can be lyophilized alone or in combination with antibiotic compounds/agents as described above optionally including any agents. The agents include complexing agents or anticoagulants, antioxidants, stabilizers, aminoglycosides, pharmaceutically acceptable salts and the like or mixtures thereof. The lyophilization can be performed for dilute solutions or concentrated solutions depending on the required quality of the final product. Prior to lyophilization or freeze-drying or thawing, the lyophilizate can be degassed to optimum concentration of gas. The compounds can be filtered under sterile condition. Appropriate filters such as ultrafiltration could also be used in order to reduce the levels of galactomannan substantially. The compounds of formula (I) could also be physically blended with a suitable antibiotic agent.

The compound of formula (I) can also be used for treating infections caused by bacteria producing β-lactamases, in particular, KPC-2.

In addition to the compound of formula (I), the pharmaceutical composition may also contain buffers like sodium citrate, sodium acetate, sodium tartrate, sodium carbonate, sodium bicarbonate, morpholinopropanesulfonic acid, other phosphate buffers and the like and chelating agents like ethylenediaminetetraacetic acid (EDTA), diethylenetriaminepentaacetic acid, hydroxyethylenediaminetriacetic acid, nitrilotriacetic acid, 1,2-diaminocyclohexanetetraacetic acid, bis(2-aminoethyl)ethyleneglycoltetraacetic acid, 1,6-hexamethylenediaminetetraacetic acid and the like or pharmaceutically acceptable salts thereof. Compounds of formula (I) are useful in treating or preventing a bacterial infection in a host, typically an animal and most typically a human, including administering to the host a therapeutic amount of compound of formula (I) or a pharmaceutically acceptable salt and/or prodrug therein along with β-lactam antibiotic.

The term "prophylaxis" or "prevention" means preventing the disease, i.e., causing the clinical symptoms of the disease not to develop.

The term "treatment"/"treating" means any treatment of a disease in a mammal, including: (a) Inhibiting the disease, i.e., slowing or arresting the development of clinical symptoms; and/or (b) Relieving the disease, i.e., causing the regression of clinical symptoms.

The term "therapeutically effective amount" or "effective amount" refers to that amount of a compound or mixture of compounds of formula (I) that is sufficient to effect treatment, as defined below, when administered alone or in combination with other therapies to a mammal in need of such treatment.

The term "potentiating" refers to the enhancement of the effects of an agent by another agent so that the total effect is greater than the sum of the effects of either agent.

The term "compound(s) for use" as used herein embrace any one or more of the following: (1) use of compound(s), (2) method of use of compound(s), (3) use in the treatment of, (4) the use for the manufacture of pharmaceutical composition/medicament for treatment/treating or (5) method of treatment/treating/preventing/reducing/inhibiting comprising administering an effective amount of compound of formula (I) to a subject in need thereof.

The term 'subject' refers to patients with bacterial infections, preoperative patients, postoperative patients, patients in ICU, patients with nosocomial infections, community acquired infections and veterinaries.

From the foregoing description, one skilled in the art can easily ascertain the essential characteristics of this invention and without departing from the spirit and scope thereof make various changes and modifications of the invention to adapt it to various usages and conditions.

A term once described, the same meaning applies for it throughout the patent.

Reference Compound-1 (Compound-1)

1-{[(2S,3S,5R)-2-Carboxy-3-methyl-4,4,7-trioxo-4-thia-1-azabicyclo[3.2.0]hept-3-yl]methyl}-3-methyl-1H-1,2,3-triazol-3-ium

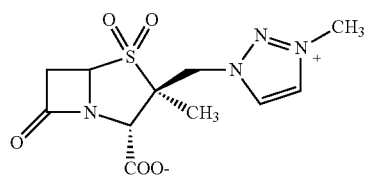

To a suspension of (2S,3S,5R)-3-methyl-7-oxo-3-(1H-1,2,3-triazol-1-ylmethyl)-4-thia-1-azabicyclo-[3.2.0]heptane-2-carboxylic acid 4,4-dioxide (25 g) in acetone (100 mL) at 25-30° C. was added slowly N,O-bis(silyl)acetamide (18.6 g) with stirring. The reaction mixture was stirred at this temperature (25-30° C.) for 15-20 minutes. To the clear solution obtained, methyl iodide (100 mL) was added over a period of 15 minutes and stirred at 25-30 minutes for 24 hours. The precipitated solid was separated by filtration and washed with acetone (25 mL). Wet weight of the solid obtained was 30 g.

The above wet solid was stirred with purified water (300 mL) at 10-15° C. for 2.5 hours. To the resulted reaction mixture was added sodium thiosulfate (0.1 g) and stirred at 10-15° C. for 10-15 minutes. To the reaction mixture, dichloromethane (300 mL) was added, stirred and the organic layer was separated. The aqueous layer was washed with a solution of Amberlite LA-2 resin (5% solution in dichloromethane twice, followed by dichloromethane twice. To the aqueous solution, activated carbon (1 g) was added, stirred for 15 minutes, filtered and washed with purified water (25 mL). The solution was filtered and lyophilized to get the title compound in pure form (10 g). $^1$H NMR (400 MHz, DMSO-$d_6$) δ ppm: 1.39 (s, 3H), 3.14 (dd, J=16.0, 1.3 Hz, 1H), 3.55 (dd, J=16.0, 4.2 Hz, 1H), 3.97 (s, 1H), 4.34 (s, 3H), 5.05 (dd, J=4.2, 1.3 Hz, 1H), 5.29 (d, J=14.7 Hz, 1H), 5.42 (d, J=14.7 Hz, 1H), 8.91 (d, J=1.3 Hz, 1H), 8.99 (d, J=1.3 Hz, 1H). Mass m/z: M+1 peak at 315. Alternatively the solution could be subjected to spray-drying to yield the title compound.

Compound-12

(2S,3S,5R)-3-Methyl-3-(3-methyl-imidazol-3-ium-1-ylmethyl)-4,4,7-trioxo-4-thia-1-azabicyclo[3.2.0]heptane-2-carboxylate Step 1: Preparation of (2S,3S,5R)-3-(imidazol-1-ylmethyl)-3-methyl-7-oxo-4-thia-1-aza-bicyclo[3.2.0]heptane-2-carboxylic acid benzhydryl ester

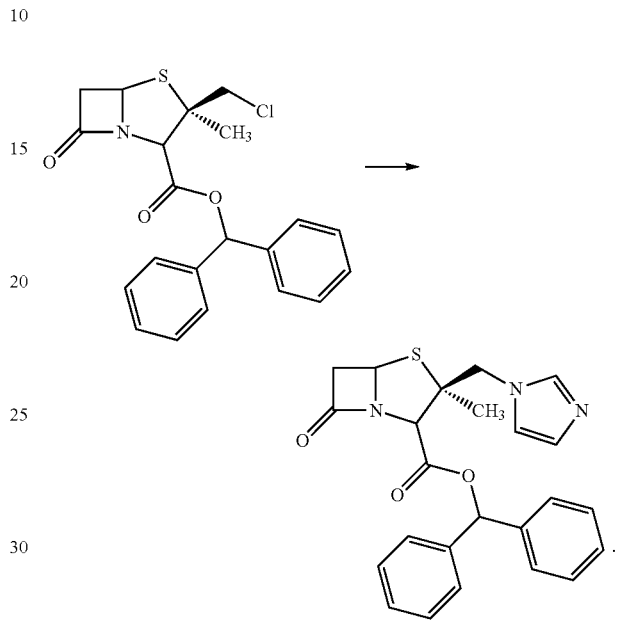

To a stirred solution of imidazole (1.696 g, 24.9 mmol) in acetonitrile (75 mL) and water (25 mL) was added sodium bicarbonate (4.18 g, 49.8 mmol) and the resultant mass was stirred for 15 minutes. (2S,3S,5R)-3-Chloromethyl-3-methyl-7-oxo-4-thia-1-aza-bicyclo[3.2.0]heptane-2-carboxylic acid benzhydryl ester (10 g, 24.8 mmol) was added to the above mixture and stirred at 25-30° C. for 24 hours. After the completion of the reaction, the reaction mass was diluted with ethyl acetate and water mixture. The organic layer was separated. The aqueous layer was again extracted with ethyl acetate. The combined organic layer was dried over anhydrous sodium sulphate and concentrated under vacuum to yield crude (2S,3S,5R)-3-(imidazol-1-ylmethyl)-3-methyl-7-oxo-4-thia-1-aza-bicyclo[3.2.0]heptane-2-carboxylic acid benzhydryl ester. Yield: 10 g.

Step 2: Preparation of (2S,3S,5R)-3-(imidazol-1-ylmethyl)-3-methyl-4,4,7-trioxo-4-thia-1-aza-bicyclo[3.2.0]heptane-2-carboxylic acid benzhydryl ester

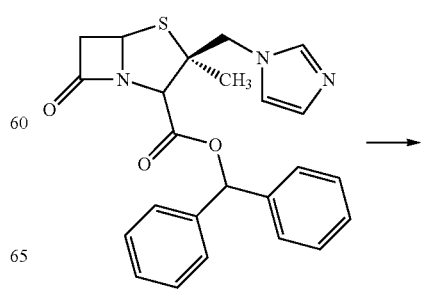

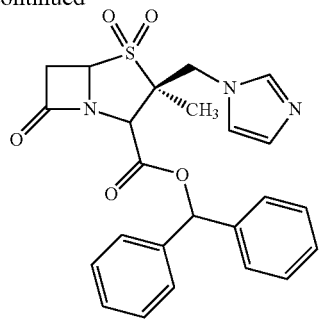

The crude (2S,3S,5R)-3-(imidazol-1-ylmethyl)-3-methyl-7-oxo-4-thia-1-aza-bicyclo[3.2.0]heptane-2-carboxylic acid benzhydryl ester (10 g) obtained in the previous step was dissolved in acetonitrile (50 mL). Acetic acid and water mixture was added to the above solution and was cooled to 0-5° C. To the homogeneous reaction mixture potassium permanganate (14.59 g, 92.3 mmol) was added. Stirring was continued at 0-5° C. for another 2 hours. The reaction mass was quenched with sodium metabisulphite solution. The reaction mass was diluted with ethyl acetate and water mixture. The organic layer was separated and the aqueous layer was extracted with ethyl acetate. The combined organic layer was neutralised with saturated sodium bicarbonate solution. The organic layer was dried over anhydrous sodium sulphate and concentrated under reduced pressure. Acetone was added to the residue obtained and stirred for 30 minutes. A white solid precipitated out, which was filtered and dried. Yield: 2.60 g (22.4%). $^1$H NMR (400 MHz, DMSO-$d_6$) δ ppm: 1.09 (s, 3H), 3.35 (d, J=16.0 Hz, 1H), 3.76 (dd, J=16.0, 2.0 Hz, 1H), 4.42 (d, J=15.6 Hz, 1H), 4.90 (d, J=15.6 Hz, 1H), 5.10 (s, 1H), 5.26 (m, 1H), 6.89 (s, 2H), 6.98 (s, 1H), 7.33-7.50 (m, $^1$H). Mass m/z: 466 (M+1).

Step-3: Preparation of (2S,3S,5R)-3-(imidazol-1-ylmethyl)-3-methyl-4,4,7-trioxo-4-thia-1-aza-bicyclo[3.2.0]heptane-2-carboxylic acid (Compound-M)

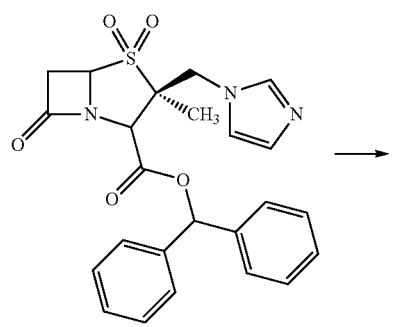

To a solution of (2S,3S,5R)-3-(imidazol-1-ylmethyl)-3-methyl-4,4,7-trioxo-4-thia-1-aza-bicyclo[3.2.0]heptane-2-carboxylic acid benzhydryl ester (900 mg, 1.9 mmol) in methanol (20 mL) was added 10% Pd/C (900 mg w/w) and stirred under hydrogen atmosphere for 2 hours. The reaction mass was filtered and washed with methanol. The filtrate was evaporated under reduced pressure. To the residue was added diethyl ether (30 mL) and stirred for 15 minutes. The white solid precipitated out was filtered and washed with diethyl ether. Yield: 530 mg (91.3%). $^1$H NMR (400 MHz, DMSO-$d_6$) δ ppm: 1.38 (s, 3H), 3.28 (d, J=16.4 Hz, 1H), 3.68 (dd, J=16.4, 4.4 Hz, 1H), 4.51 (d, 15.2 Hz, 1H), 4.53 (s, 1H), 4.84 (d, J=15.2 Hz, 1H), 5.14-5.15 (m, 1H), 7.02 (s, 1H), 7.25 (s, 1H), 7.85 (s, 1H). Mass m/z: 300 (M+1).

Step 4: Preparation of (2S,3S,5R)-3-methyl-3-(3-methyl-imidazol-3-ium-1-ylmethyl)-4,4,7-trioxo-4-thia-1-azabicyclo[3.2.0]heptane-2-carboxylate

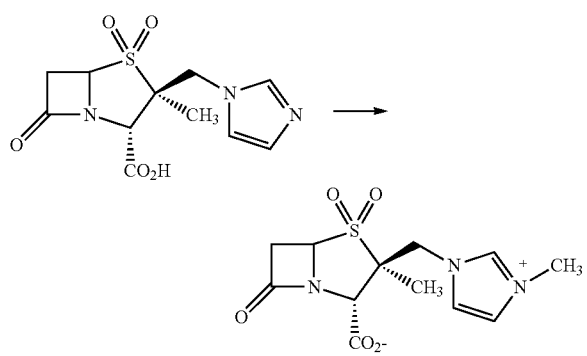

To a suspension of (2S,3S,5R)-3-(imidazol-1-ylmethyl)-3-methyl-4,4,7-trioxo-4-thia-1-aza-bicyclo[3.2.0]heptane-2-carboxylic acid (450 mg, 1.5 mmol) in dry acetone (1.8 mL) was added slowly N,O-bis(silylacetamide) (0.93 mL, 3.7 mmol) with stirring. The reaction mass was stirred further for 15 minutes. To the clear solution obtained, methyl iodide (1.8 mL) was added and stirred at 25-30° C. for 2 days. The reaction mass was concentrated and diluted with dichloromethane-water. The organic layer was separated. The aqueous layer was washed with a solution of Amberlite LA-2 resin (30% solution in dichloromethane), followed by dichloromethane. The aqueous layer was degassed and lyophilized to obtain the title compound. Melting point: 161.37° C. $^1$H NMR (400 MHz, $D_2O$) δ ppm: 1.53 (s, 3H), 3.47 (dd, J=16.7, 1.36 Hz, 1H), 3.70 (dd, J=16.7, 4.2 Hz, 1H), 3.94 (s, 3H), 4.41 (s, 1H), 4.99 (ABquartet, J=15.4 Hz, 2H), 5.09 (m, 1H), 7.53 (s, 1H), 7.64 (s, 1H), 8.99 (s, 1H). Mass m/z: 314 (M+1).

Compound 13

(2S,3S,5R)-3-Methyl-3-(4-methyl-3-methyl-imidazol-3-ium-1-ylmethyl)-4,4,7-trioxo-4-thia-1-azabicyclo[3.2.0]heptane-2-carboxylate Step 1: Preparation of (2S,3S,5R)-3-(4-methyl-imidazol-1-ylmethyl)-3-methyl-7-oxo-4-thia-1-aza-bicyclo[3.2.0]heptane-2-carboxylic acid benzhydryl ester

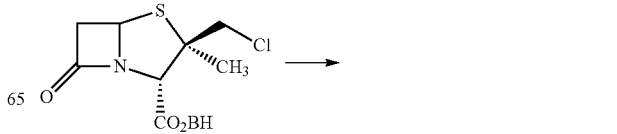

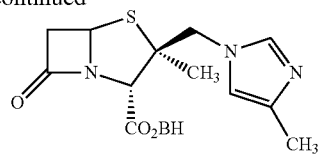

To a stirred solution of (2S,3S,5R)-3-chloromethyl-3-methyl-7-oxo-4-thia-1-aza-bicyclo[3.2.0]heptane-2-carboxylicacid benzhydryl ester (3 g, 7.4 mmol) in acetonitrile (22.5 mL)) was added sodium bicarbonate (628 mg, 7.4 mmol), water (7.5 mL) and 4-methyl-imidazole (1.22 g, 7.4 mmol). The resultant mass was stirred at 25-30° C. for 42 hours. The reaction mass was diluted with ethyl acetate and water mixture. The organic layer was separated. The aqueous layer was again extracted with ethyl acetate. The combined organic layer was dried over anhydrous sodium sulphate and concentrated under vacuum to yield crude (2S,3S,5R)-3-(4-methylimidazol-1-ylmethyl)-3-methyl-7-oxo-4-thia-1-aza-bicyclo[3.2.0]heptane-2-carboxylic acid benzhydryl ester. Yield: 3.5 g.

Step 2: Preparation of (2S,3S,5R)-3-(4-methyl-imidazol-1-ylmethyl)-3-methyl-4,4,7-trioxo-4-thia-1-aza-bicyclo[3.2.0]heptane-2-carboxylic acid benzhydryl ester

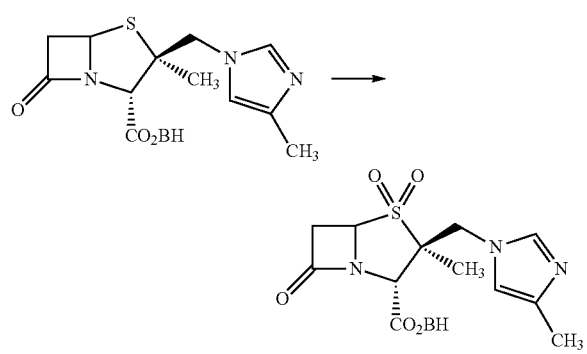

The crude (2S,3S,5R)-3-(4-methyl-imidazol-1-ylmethyl)-3-methyl-7-oxo-4-thia-1-aza-bicyclo[3.2.0]heptane-2-carboxylic acid benzhydryl ester (3.5 g, 7.8 mmol) from the previous step was dissolved in acetonitrile (18 mL). Acetic acid (18 mL) and water (9 mL) mixture was then added to the above solution and cooled to 0-5° C. To the homogeneous reaction mixture potassium permanganate (2.47 g, 15.6 mmol) was added. Stirring was continued at 0-5° C. for another 2 hours. The reaction mass was then quenched with sodium metabisulphite solution and diluted with ethyl acetate and water. The organic layer was separated and the aqueous layer was extracted with ethyl acetate. The combined organic layer was neutralised with saturated sodium bicarbonate solution. The organic layer was dried over anhydrous sodium sulphate and concentrated under reduced pressure. Purification of the crude compound using silicagel column chromatography (gradient elution with 40-50% ethyl acetate in hexane) yielded the pure compound as a colourless solid. Yield: 350 mg (10%). $^1$H NMR (400 MHz, CDCl$_3$, δ ppm): 1.00 (s, 3H), 2.17 (s, 3H), 3.50 (dd, J=16.2 Hz, 1.8 Hz, 1H), 3.57 (dd, J=16.2 Hz, 4.1 Hz, 1H), 4.24 (d, J=15.3 Hz, 1H), 4.50 (s, 1H), 4.61-4.62 (m, 1H), 6.53 (s, 1H), 6.99 (s, 1H), 7.05 (s, 1H) 7.32-7.49 (m, 10H).

Step 3: Preparation of (2S,3S,5R)-3-methyl-3-(4-methyl-3-methyl-imidazol-3-ium-1-ylmethyl)-4,4,7-trioxo-4-thia-1-aza-bicyclo[3.2.0]heptane-2-carboxylic acid benzhydryl ester

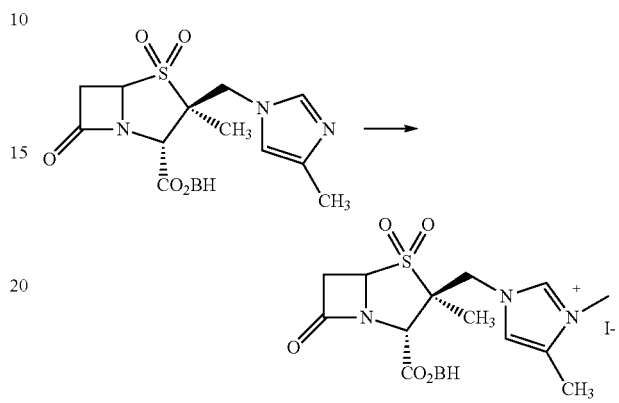

To a suspension of (2S,3S,5R)-3-(4-methyl-imidazol-1-ylmethyl)-3-methyl-4,4,7-trioxo-4-thia-1-aza-bicyclo[3.2.0]heptane-2-carboxylic acid benzhydryl ester (350 mg, 0.6 mmol) in dry acetone (4 mL) was added methyl iodide (4 mL) and stirred at 25-30° C. for 15 hours. The reaction mass was concentrated and purified using silica gel column chromatography (gradient elution with 0-10% MeOH in dichloromethane) to yield the product as a pale yellow solid. Yield: 320 mg (96%). $^1$H NMR (400 MHz, CDCl$_3$, S ppm): 1.35 (s, 3H), 2.30 (s, 3H), 3.47 (dd, J=16.4 Hz, 1.7 Hz 1H), 3.58 (dd, J=16.4 Hz, 4.4 Hz 1H), 3.89 (s, 3H), 4.6 (s, 1H), 4.69 (m, 1H), 4.89 (ABquartet, J=15.9 Hz, 2H), 7.01 (s, 1H), 7.26 (s, 1H), 7.32-7.49 (m, 10H), 9.83 (s, 1H).

Step 4: Preparation of (2S,3S,5R)-3-methyl-3-(4-methyl-3-methyl-imidazol-3-ium-1-ylmethyl)-4,4,7-trioxo-4-thia-1-aza-bicyclo[3.2.0]heptane-2-carboxylate

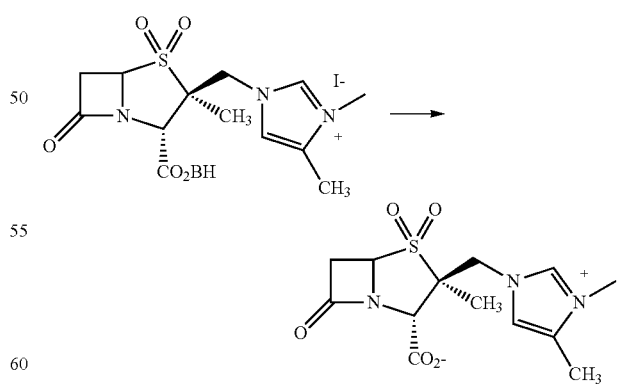

To a suspension of (2S,3S,5R)-3-methyl-3-(4-methyl-3-methyl-imidazol-3-ium-1-ylmethyl)-4,4,7-trioxo-4-thia-1-aza-bicyclo[3.2.0]heptane-2-carboxylic acid benzhydryl ester (310 mg, 0.62 mmol) was added m-cresol (3 mL) and stirred at room temperature overnight. Hexane (3×25 mL)

was added to the reaction mixture and stirred for 5 minutes then decanted. Diethyl ether (15 mL) was added to it. The solid obtained was diluted with water and treated with Amberlite LA-2 resin (30% solution in dichloromethane), followed by dichloromethane. The aqueous layer was lyophilised to yield the product as a pale yellow solid. Yield: 130 mg (75%). $^1$H NMR (400 MHz, D$_2$O) δ ppm: 1.52 (s, 3H), 2.31 (s, 3H), 3.47 (dd, J=16.7 Hz, 1.3 Hz 1H), 3.71 (dd, J=16.7 Hz, 4.1 Hz 1H), 3.80 (s, 3H), 4.39 (s, 1H), 4.92 (ABquartet, J=15.4 Hz, 2H), 5.08 (m, 1H), 7.38 (s, 1H), 8.86 (s, 1H). Mass m/z: 328 (M+1).

The examples below are provided by way of illustration only and should not be considered to limit the scope of the invention. Variation and changes, that are obvious to one skilled in the art, are intended to be within the scope and nature of the invention.

Biology:

Detection of KPC/ESBL producing Enterobacteriaceae

In this experiment, Compound-1 is used as a diagnostic reagent for the detection of β-lactamases belonging to the families KPC & ESBL (e.g., SHV18) producing Enterobacteriaceae. A simple set of absorbent paper disks impregnated with antibiotic on agar medium is used for the detection. When the bacterial strain expresses β-lactamases, the zone of inhibition in combination with Compound-1 will be significantly larger than the antibiotic alone.

Methodology 1:
  0.5 McFarland of the test organism was inoculated at 1:10 dilution on Muller
  Hinton Agar plates
  Test organisms: *Klebsiella pneumoniae* (K.p) ATCC BAA-1705, *Klebsiella pneumoniae* ATCC 700603, *Escherichia coli* (E.c) Ecoli233
  Carbapenem (e.g., Imipenem [IPM] 10 μg) and cephalosporin (e.g., Ceftazidime [CAZ] 30 μg) paper disks (7 mm) were placed on the inoculated agar plates
  Compound-1 (60 μg) disk was placed at a distance of 7 & 10 mm from the carbapenem and cephalosporin disks.
  The presence of expressed carbapenemases or ESBLs was measured as the expansion of Imipenem or Ceftazidime's inhibition zones due to synergy in the presence of Compound-1.

Results:
Synergy was observed as an increase of the Imipenem or Ceftazidime zone adjacent to Compound-1 containing disk (FIG. 1).

Methodology 2:
The methodology remains the same as Methodology 1 except the following change
  Compound-1 (60 μg) was added on the same disk in combination with a carbapenem (e.g., Imipenem 10 μg) or cephalosporin (e.g., Ceftazidime 30 μg) and placed on the inoculated agar plate.
  The presence of the expressed carbapenemases or ESBLs was measured as an increase in Imipenem or Ceftazidime's zone diameter in combination with Compound-1 compared to antibiotic alone.

Results

The inhibitory activity of Compound-1 on carbapenemases or ESBLs was demonstrated by an increase in the zone diameter (Table 1) of Imipenem or Ceftazidime in combination with Compound-1 compared to antibiotic alone (FIG. 1). Methodology 1 in figures (A), (B) & (C) show an increase in the zone of inhibition of Imipenem or Ceftazidime adjacent to compound-1 containing disk when kept at a distance of 10 mm and 7 mm, Methodology 2 in figures (A), (B) & (C) show an increase in the zone of inhibition of Imipenem or Ceftazidime in combination with compound-1 (IT & CT) rather than the antibiotic alone (I & C). Both the methods in (D) do not show increase in the zone of inhibition and that compound-1 does not show any zone of inhibition, due to the absence of β-lactamase in the strain. Results for Isolates with KPC Enzymes are Shown in Table 1.

TABLE 1

Zone of inhibition (ZOI) for clinical isolates with class A carbapenemases and ESBL

| | | | ZOI (mm) | | | |
|---|---|---|---|---|---|---|
| | | | CAZ | | IPM | |
| Phenotype | Organism | Strain ID | Alone | + Compound-1 | Alone | + Compound-1 |
| KPC2 | *K. pneumoniae* | ATCC BAA-1705 | 12 | 18.5 | 14.5 | 20 |
| KPC3 | *E. coli* | Ecoli233 | 11 | 22.5 | 14 | 20 |
| SHV18 | *K. pneumoniae* | ATCC 700603 | 12 | 23 | 25 | 25 |
| β-lac-ve | *E. coli* | ATCC 25922 | 25 | 25 | 26.5 | 26.5 |

Compound-1 increased the zone of inhibition of Ceftazidime from 12 to 18.5 mm and 11 to 22.5 mm against the tested KPC2 and KPC3 producing strains respectively.

Compound-1 increased the zone of inhibition of Imipenem from 14.5 to 20 mm and 14 to 20 mm against the tested KPC2 and KPC3 producing strains respectively.

Compound-1 increased the zone of inhibition of Ceftazidime from 12 to 23 mm against the tested SHV18 producing strain while there was no change in the diameter of Imipenem with or without Compound-1 indicating, the inherent activity of Imipenem against this strain.

Against the β-lactamase negative strain, there is no impact of Compound-1 either on Ceftazidime or Imipenem since both these antibiotics have inherent activity against this strain.

Conclusion:

Compound-1 can be used as a diagnostic tool for the detection of β-lactamases including KPC.

In Vitro Testing

The β-lactam compounds of formula (I) described herein were assessed in combination with β-lactam antibiotics for its potential as β-lactamase inhibitor against carbapenemase enzymes. The compounds described herein were assessed in vitro for antibacterial activity against for example KPC producing & KPC expressing bacterial gram negative strains, β-lactamase inhibitory assay with these enzymes. The β-lactam compounds having a substitution on the heterocyclyl nitrogen atom(s) show significant β-lactamase inhibiting property. For comparative studies, Tazobactam, Clavulanic acid and Sulbactam were used along with the β-lactam antibiotics. Carbapenems, Cephalosporins, Monobactams and Penems (including those of veterinary use) were chosen as the antibacterial agents.

In Vitro Antimicrobial Testing by Determining the Minimum Inhibitory Concentration (MIC): Broth Micro Dilution Method The β-lactam compound was tested for in vitro antibacterial activities by the broth micro-dilution or agar dilution method as specified in documents published by Clinical and Laboratory Standards Institute (CLSI), USA (formerly NCCLS). Approved standard M7-A7, January 2006, CLSI, Wayne, Pa., USA and M100-S18, January 2008, CLSI, Wayne, Pa., USA.

Synergistic broth micro-dilution MIC was done in checkerboard format with a range of concentrations of the antibacterial agents along with several concentrations of the BLI compounds and other comparator BLI agents in 96 well microtitre plates. Briefly, stock solutions (e.g. 2560 & 1280 μg/mL) of the β-lactam antibiotics is made in water, 0.1 M Phosphate buffer, pH 6.0 or pH 7.0 or appropriate solvents accordingly. Similarly stock solutions of the BLI agents including the compound-1 were made. β-lactam antibiotics were screened in a concentration range of 0.06-128 μg/mL. BLI agents including the BLI compounds were tested in a concentration range of 1-64 μg/mL. Working solutions of all were made by appropriate dilutions in cation adjusted Mueller Hinton broth (caMHB). Two fold dilutions of the antibacterial agents were done from the working solutions in caMHB serially in the wells of the 96 well microtitre plates. BLI agents including the BLI compounds were also serially diluted and then each concentration to be tested was added to each of the different antibacterial concentration. The BLI compounds, other comparator BLIs and all the antibacterial agents were also tested individually. The bacterial inoculum was prepared by picking 3 to 5 well isolated bacterial colonies with the same morphological appearance from an 18-24 h old culture and adjusting the turbidity of the saline suspension to 0.5 McFarland turbidity standard equivalent to a bacterial population of $\sim 1\times 10^8$ colony forming units (CFU) per mL of suspension. The suspension was diluted 1:100 in caMHB to get a bacterial population of $\sim 1\times 10^6$ CFU/mL as inoculum. This bacterial inoculum was added into the wells of the microtitre plate containing caMHB with antibacterials or antibacterials+BLI agents in equal volume to the volume of the caMHB with antibacterials or antibacterials+BLI agents. Hence, the final inoculum becomes half ($5\times 10^5$ CFU/mL) and the concentrations of the tested antibacterials and combinations also becomes half. The inoculated plates were incubated at 35° C. in an ambient atmosphere for 18-20 h. The plates after incubation were observed with naked eye with the aid of optical mirror and MIC was recorded as the concentration, which showed no growth or visual turbidity of the inoculated culture.

In agar dilution method briefly, stock solutions of the cephalosporins for veterinary use (e.g. 2 mg/mL) was made in water, 0.1M phosphate buffers or appropriate solvents and the solution was serially two fold diluted. Compound-1 was dissolved in water and Tazobactam (comparator BLI) in 0.1M phosphate buffer, pH 6.0 to get a solution of 1 mg/mL. Cephalosporins were screened in a concentration range of 0.5-32 μg/mL. For combination, Tazobactam or the Compound-1 described herein were tested at a fixed concentration of 4 μg/mL along with the cephalosporins concentration ranging from 0.5 to 32 μg/mL. Cephalosporins alone and in combination with the compound-1 or Tazobactam from each concentration was added to 20 mL of molten Mueller Hinton agar that has been cooled to 40-50° C. and poured in petri dishes. The compound of formula (I) and Tazobactam were also tested individually. The bacterial inoculum was prepared by picking 3 to 5 well isolated bacterial colonies with the same morphological appearance from an 18-24 h old culture and adjusting the turbidity of the saline suspension to 0.5 McFarland turbidity standard equivalent to a bacterial population of $\sim 1\times 10^8$ CFU per mL of suspension. The suspension was diluted 1:10 in saline to get a bacterial population of $\sim 1\times 10^7$ CFU/mL as inoculum. This bacterial inoculum was inoculated onto the prepared petri dishes by a multipoint inoculator with each inoculum spot containing $\sim 1\times 10^4$ CFU of the bacterial strain. The inoculated petri dishes were incubated at 35° C. in an ambient atmosphere for 18-20 h. The petri dishes after incubation were placed on a dark non-reflecting surface and the MIC was recorded as the concentration, which showed no growth of the inoculated culture.

TABLE 2

Minimum inhibitory concentration (MIC) of Imipenem in combination with β-lactamase inhibitor (BLI) Compound-12 against *Klebsiella pneumoniae* carbapenemase (KPC) producing strains

| | | | MIC (μg/mL) of imipenem in combination with BLI at 4 or 16 μg/mL | | | | | | | | |
|---|---|---|---|---|---|---|---|---|---|---|---|
| KPC | | No | Compound-13 | | Compound-M | | Compound-12 | | Compound-1 | | Tazobactam | |
| type | Strains | BLI | 4 | 16 | 4 | 16 | 4 | 16 | 4 | 16 | 4 | 16 |
| KPC2 | K. pneumoniae ATCC BAA-1705 | 32-64 | 2 | 2 | 8 | 8 | 4 | 4 | 4 | <0.5-1 | 16 | 8 |
| KPC2 | K. pneumoniae UMM3 | 8 | NA | NA | 8 | NA | 2 | NA | 1 | NA | 4 | NA |
| KPC2* | E. cloacae 01 MGH 049 | 8 | NA | NA | 8 | NA | 8 | NA | 4 | NA | 8 | NA |
| KPC3 | E. coli Ecoli233 | 16 | 8 | 1 | 16 | 16 | 4 | 1 | 4 | 1 | 8 | 8 |
| KPC3 | K. pneumoniae NCTC 13438 | 128 | NA | NA | 64 | NA | 64 | NA | 32 | NA | 64 | NA |

NA: Not available
*Presence of AmpC was observed phenotypically

Compound-12 shows improved activity against the KPC (2 & 3) producing strains within the range similar to Compound-1, while Compound-M is only moderately active not within the expected range of activity.

TABLE 3a

MIC of Penems or Monobactam/Compound-1 against KPC-2 producing *K. pneumoniae* (ATCC BAA-1705)

| BLI | BLI conc. (µg/mL) | IMP | MER | ERT | FAR | AZT | BLI |
|---|---|---|---|---|---|---|---|
| BLI |  | 32-64 | 32-64 | >64 | >64 | >64 |  |
| + Compound-1 | 2 | 4-8 | 16 | NA | NA | NA | >64 |
|  | 4 | 4 | 4-8 | 32 | >64 | >64 |  |
|  | 8 | 2 | 2-4 | 16 | >64 | NA |  |
|  | 16 | 1 | 1 | 8 | 64 | 64 |  |
|  | 64 | <0.5-1 | <0.5 | <0.5 | 4 | <0.5 |  |
| + Tazobactam | 2 | 16 | 32 | NA | NA | NA | >64 |
|  | 4 | 16 | 32 | >64 | >64 | >64 |  |
|  | 8 | 8-16 | 16-32 | >64 | >64 | NA |  |
|  | 16 | 8 | 8-16 | 64 | >64 | >64 |  |
|  | 64 | 4-8 | 4 | 32 | >64 | >64 |  |
| + Clavulanic acid | 2 | 8-16 | 16 | 32 | >64 | NA | >64 |
|  | 4 | 8-16 | 4-8 | 64 | >64 | >64 |  |
|  | 8 | 4-8 | 4 | NA | NA | NA |  |
|  | 16 | 2 | 4 | 32 | >64 | >64 |  |
|  | 64 | <0.5 | 2 | 8 | >64 | 64 |  |
| + Sulbactam | 2 | 16-32 | 32 | NA | NA | NA | >64 |
|  | 4 | 16-32 | 32 | >64 | >64 | >64 |  |
|  | 8 | 16 | 32 | >64 | >64 | NA |  |
|  | 16 | 8 | 32 | >64 | >64 | >64 |  |
|  | 64 | 8 | 16 | 64 | >64 | >64 |  |

IMP: Imipenem, MER: Meropenem, ERT: Ertapenem, FAR: Faropenem & AZT: Aztreonam.

Compound-1 synergized with Imipenem and Meropenem better than Tazobactam or Clavulanic acid or Sulbactam against KPC-2 producing strain ATCC BAA1705 at ≥4 µg/mL concentration. It also showed better synergy with Ertapenem, Faropenem and Aztreonam than the above comparators at 64 µg/mL concentration (Table-3a). Similarly, the following compounds in the series showed the restoration of antibacterial activity of Imipenem & Meropenem (Table-3b).

TABLE 3b

Penems BLI compounds against KPC-2 producing *K. pneumoniae* (ATCC BAA-1705)

|  | BLI conc. (µg/mL) | Imipenem 32-64 | Meropenem 32-64 | BLI |
|---|---|---|---|---|
| BLI |  |  |  |  |
| Compound-4 | 4 | 4 | 8 | >16 |
|  | 16 | 1 | 4 |  |
| Compound-2 | 4 | 4 | 8 | >16 |
|  | 16 | 1 | 2 |  |
| Compound-6 | 4 | 8 | 16 | >16 |
|  | 16 | 8 | 4 |  |
| Compound-5 | 4 | 8 | 8 | >16 |
|  | 16 | 1 | 2 |  |
| Compound-8 | 4 | 8 | 8 | >16 |
|  | 16 | 4 | 4 |  |
| Compound-1 | 4 | 4 | 8 | >16 |
|  | 16 | 1 | 1 |  |
| Tazobactam | 4 | 16 | 32 | >16 |
|  | 16 | 8 | 8-16 |  |

TABLE 4

Human cephalosporins/compound-1 against KPC-2 producing *K. pneumoniae* (ATCC BAA-1705)

|  | BLI conc. (µg/mL) | CEF | CTX | CTZ | CTB | BLI |
|---|---|---|---|---|---|---|
| BLI |  | >128 | >128 | >128 | >64 |  |
| + Compound-1 | 2 | 64 | 32 | >64 | >64 | >64 |
|  | 4 | 32 | 16 | ≥64 | >64 |  |
|  | 8 | 16 | 16 | 64 | >64 |  |
|  | 16 | 4 | 4 | 4 | 64 |  |
|  | 64 | <0.5 | ≤0.5 | 1 | ≤0.5 |  |
| + Tazobactam | 2 | 64 | ≥64 | >64 | >64 | >64 |
|  | 4 | 64 | 32-64 | >64 | >64 |  |
|  | 8 | 32 | 32 | >64 | >64 |  |
|  | 16 | 32 | 32 | >64 | >64 |  |
|  | 64 | 32 | 32 | 64 | >64 |  |
| + Clavulanic acid | 2 | 64 | 32-64 | >64 | >64 | >64 |
|  | 4 | 64 | 32-64 | >64 | >64 |  |
|  | 8 | 32 | 16-32 | >64 | >64 |  |
|  | 16 | 32 | 16 | 64 | >64 |  |
|  | 64 | 8 | 8 | 16 | 64 |  |
| + Sulbactam | 2 | >64 | >64 | >64 | >64 | >64 |
|  | 4 | ≥64 | >64 | >64 | >64 |  |
|  | 8 | 64 | 64 | >64 | >64 |  |
|  | 16 | 64 | 32 | >64 | >64 |  |
|  | 64 | 64 | 32 | 64 | >64 |  |

CEF: Cefepime, CTX: Cefotaxime, CTZ: Ceftazidime & CTB: Ceftobiprole

Compound-1 synergized with Cefepime better than Tazobactam or Clavulanic acid or Sulbactam against KPC-2 producing strain ATCC BAA1705 at ≥16 µg/mL concentration. It also showed better synergy with Cefotaxime & Ceftazidime than the above comparators at 64 µg/mL concentration. Ceftobiprole did not show any synergy at the tested conc. against all the compared compounds (Table-4).

TABLE 5

Veterinary cephalosporins/compound-1 against KPC-2 producing *K. pneumoniae* (ATCC BAA-1705)

|  | BLI conc. (µg/mL) | CFQ | CFF | CFD | CFL | BLI |
|---|---|---|---|---|---|---|
| BLI |  | >64 | >64 | >64 | >64 |  |
| + Compound-1 | 1 | >64 | >64 | NA | NA | >64 |
|  | 2 | >64 | >64 | NA | NA |  |
|  | 4 | 64 | >64 | >64 | >64 |  |
|  | 8 | 64 | 64 | NA | NA |  |
|  | 16 | 8-16 | 16-32 | >64 | 32 |  |
|  | 32 | 2-4 | 4 | NA | NA |  |
|  | 64 | 1 | 2-4 | 64 | 8 |  |
| + Tazobactam | 1 | >64 | >64 | NA | NA | >64 |
|  | 2 | >64 | >64 | NA | NA |  |
|  | 4 | >64 | >64 | >64 | >64 |  |
|  | 8 | 64 | >64 | NA | NA |  |
|  | 16 | 64 | >64 | >64 | >64 |  |
|  | 32 | 64 | 64 | NA | NA |  |
|  | 64 | 64 | 64 | >64 | >64 |  |

CFQ: Cefquinome, CFF: Ceftiofur, CFD: Cefadroxil & CFL: Cefalonium

Compound-1 synergized with cephalosporins for veterinary use Cefquinome and Ceftiofur better than Tazobactam against KPC-2 producing strain ATCC BAA1705 at ≥32 µg/mL concentration. Cefadroxil & Cefalonium did not show the desired synergy at the tested concentrations (Table-5).

TABLE 6a

Carbapenems & human cephalosporins/compound-1 against KPC-3 expressing *E. coli* (J53 R6206)

| BLI | BLI conc. (µg/mL) | IMP | MER | CEF | CTX | CTZ | CTB | BLI |
|---|---|---|---|---|---|---|---|---|
| | | 2-4 | 2-4 | >16 | >32 | >32 | >32 | |
| + Compound-1 | 2 | 1 | <0.06 | 1 | 1 | 2 | 2 | >8 |
| | 4 | 0.5 | <0.06 | 0.25 | <0.25 | 1 | 0.5 | |
| | 8 | 0.5 | <0.06 | <0.125 | <0.25 | 1 | <0.25 | |
| + Tazobactam | 2 | 2 | 1 | 16 | 8 | 32 | 32 | >8 |
| | 4 | 2 | 0.5 | 8 | 8 | 32 | 16 | |
| | 8 | 1 | 0.5 | 4 | 4 | 32 | 16 | |
| + Clavulanic acid | 2 | 1 | 1 | 8 | 4 | 32 | 8 | >8 |
| | 4 | 1 | 1 | 8 | 1 | 32 | 8 | |
| | 8 | 0.5 | 0.5 | 1 | <0.25 | 8 | 2 | |
| + Sulbactam | 2 | 4 | 2 | 16 | >32 | 32 | 32 | >8 |
| | 4 | 2 | 1 | 16 | 16 | 32 | 32 | |
| | 8 | 2 | 1 | 8 | 8 | 32 | 16 | |

IMP: Imipenem, MER: Meropenem, CEF: Cefepime, CTX: Cefotaxime, CTZ: Ceftazidime & CTB: Ceftobiprole Compound-1 synergized with Imipenem, Meropenem, Cefepime, Cefotaxime, Ceftazidime and Ceftobiprole better than Tazobactam or Clavulanic acid or Sulbactam against KPC-3 expressing *E. coli* strain J53 R6206 at ≥2 µg/mL concentration (Table-6a). Similarly, the following compounds in the series showed the restoration of antibacterial activity of Imipenem & Meropenem (Table-6b)

TABLE 6b

Carbapenems BLI compounds against KPC-3 expressing *E. coli* (J53 R6206)

| BLI | BLI conc. (µg/mL) | Imipenem 2-4 | Meropenem 2-4 | BLI |
|---|---|---|---|---|
| | | MIC (µg/mL) | | |
| Compound-4 | 4 | 0.5 | <0.125 | >16 |
| | 16 | 0.25 | <0.125 | |
| Compound-2 | 4 | 0.5 | <0.125 | >16 |
| | 16 | 0.25 | <0.125 | |
| Compound-6 | 4 | 1 | 0.5 | >16 |
| | 16 | 0.5 | <0.125 | |
| Compound-5 | 4 | 0.5 | <0.125 | >16 |
| | 16 | 0.25 | <0.125 | |
| Compound-8 | 4 | 1 | 0.25 | >16 |
| | 16 | 0.25 | <0.125 | |
| Compound-1 | 4 | 0.5 | <0.125 | >16 |
| | 16 | 0.25 | <0.125 | |
| Tazobactam | 4 | 2 | 0.5 | >16 |
| | 16 | 1 | <0.125 | |

TABLE 7

Veterinary cephalosporins/Compound-1 against KPC-3 expressing *E. coli* (J53 R6206)

| BLI | BLI conc. (µg/mL) | CFQ | CFF | CFD | CFL | BLI |
|---|---|---|---|---|---|---|
| | | MIC (µg/mL) | | | | |
| BLI | | 16 | 16 | >32 | 32 | |
| + Compound-1 | 4 | <0.5 | <0.5 | >32 | 4 | >16 |
| + Tazobactam | 4 | 8 | 2 | >32 | 32 | >16 |

CFQ: Cefquinome, CFF: Ceftiofur, CFD: Cefadroxil & CFL: Cefalonium

Compound-1 synergized with Cephalosporins for veterinary use Cefquinome Ceftiofur & Cefalonium better than Tazobactam against KPC-3 expressing *E. coli* strain J53 R6206 at 4 µg/mL concentration. Cefadroxil did not show the desired synergy at the tested concentrations (Table-7).

β-Lactamase Inhibitory Assay with Carbapenemases

The Compound-1 was subjected to β-lactamase inhibitory assay to determine $IC_{50}$ and to compare that with the comparator BLI agents as described elsewhere (Bebrone et. al., *Antimicrob. Agents. Chemother,* 2001, 45(6): 1868-1871; Jamieson et. al, *Antimicrob. Agents. Chemother,* 2003, 47(5): 1652-1657). Briefly, enzyme extracts from KPC-2 producing and KPC-3 expressing bacterial gram negative strains were used to study the β-lactamase inhibitory activity and determination of $IC_{50}$ using CENTA as the substrate for β-lactamase.

TABLE 8

β-lactamase enzyme inhibitory assay of Compound-1 with carbapenemases

| BLI | $IC_{50}$ (µM) | |
|---|---|---|
| | KPC2 | KPC2 |
| Compound-1 | 190 | 10.7 |
| Tazobactam | 980 | 71 |
| Clavulanic acid | 330 | 92 |
| Sulbactam | 1400 | 235 |

The $IC_{50}$ of compound-1 is lower than the compared BLIs against the crude KPC-2 & 3 enzyme extracts indicating its superior binding hence potency of the BLI of compound-1 of formula (I) (Table-8).

TABLE 9

Comparison of MIC (µg/mL) of Piperacillin in combination with standard Tazo and Novel Inhibitor compounds against specific Extended spectrum β-lactamase (ESBLs) producing Gram-negative isolates from ATCC

| | | MIC of Piperacillin with different concentrations of Tazo or Compound-12 Inhibitor Conc.: | | | | | | | | |
|---|---|---|---|---|---|---|---|---|---|---|
| | ESBL | 1 µg/mL | | | 2 µg/mL | | | 4 µg/mL | | |
| ATCC strains | Phenotype | Tazo | Compound-M | Compound-12 | Tazo | Compound-M | Compound-12 | Tazo | Compound-M | Compound-12 |
| *E. coli* BAA-201 | TEM-3 | 4 | 4 | 2 | 4 | 4 | 4 | 2 | 4 | 4 |
| *E. coli* BAA-197 | TEM-12 | 64 | 4 | 4 | 8 | 8 | 4 | 4 | 4 | 4 |
| *E. coli* BAA-198 | TEM-26 | 4 | 4 | 4 | 4 | 4 | 4 | 4 | 4 | 4 |
| *P. mirabilis* BAA-663 | TEM-89 | 8 | 64 | 8 | 8 | >128 | 16 | 4 | >128 | >128 |
| *E. coli* BAA-199 | SHV-3 | >128 | >128 | >128 | >128 | >128 | >128 | >128 | >128 | 2 |

TABLE 9-continued

Comparison of MIC (µg/mL) of Piperacillin in combination with standard Tazo and Novel Inhibitor compounds against specific Extended spectrum β-lactamase (ESBLs) producing Gram-negative isolates from ATCC

| | | MIC of Piperacillin with different concentrations of Tazo or Compound-12 Inhibitor Conc.: | | | | | | | |
|---|---|---|---|---|---|---|---|---|---|
| | ESBL | 1 µg/mL | | | 2 µg/mL | | | 4 µg/mL | |
| ATCC strains | Phenotype | Tazo | Compound-M | Compound-12 | Tazo | Compound-M | Compound-12 | Tazo | Compound-M | Compound-12 |
| E. coli BAA-200 | SHV-4 | >128 | >128 | 32 | >128 | >128 | 8 | 4 | >128 | 4 |
| K. pneumoniae 700603 | SHV-18 | 16 | 16 | 8 | 16 | 32 | 16 | 16 | 16 | 8 |

In Vivo Efficacy of Compound-1 Against KPC Carbapenemase Producing Strains

The Compound-1 is a potent inhibitor of ESBLs and its inhibitory activity against KPC enzymes was demonstrated in vitro. Compound-1 was evaluated against KPC2 producing K. pneumoniae ATCC BAA 1705 in the pharmacodynamics models of mice systemic infection and thigh infection for in vivo translation of its inhibitory activity against KPC2. In these models, efficacy of β-lactams as single agents deteriorated due to KPC2 mediated hydrolysis. By combining compound-1 with β-lactams, its potential to restore or enhance the efficacy of β-lactams was assessed.

Method:

Mice Systemic Infection Model

Female Swiss Albino mice, weighing 18-22 g were used for all studies. For each dose group, 5 or 6 mice were included. Study protocols were reviewed and approved by Institutional Animal Ethical Committee, Orchid Research Laboratories Limited. Mice were housed in individually ventilated cages provided with food and water ad libitum, throughout the study period. From overnight culture in Brain-Heart Infusion agar medium, challenge inoculum with required bacterial density was prepared in normal saline containing Hog gastric mucin. In studies involved with doripenem, washed bacterial cells was used. Each mouse was infected with of challenge inoculum by intra-peritoneal injection.

Piperacillin with β-lactamase inhibitor (BLI) combinations: Increasing concentrations of piperacillin and BLIs (Compound-1 or tazobactam) as single agents or piperacillin in combination with BLIs at 1:1 ratio were prepared in aqueous agar (Bacto agar). Infected mice were dosed sub-cutaneously, with drug preparations at three different time points post-infection.

Imipenem with BLI combinations: Increasing concentrations of Imipenem as single agent or in combination with fixed concentration of BLIs were used to dose infected mice, sub-cutaneously. In this experiment Imipenem was always administered along with cilastatin.

Doripenem with BLI combinations: Increasing concentrations of doripenem as single agent or in combination with fixed concentration of BLIs were used to dose infected mice, sub-cutaneously.

Survival of the treated mice were monitored twice a day, up to 7 days post-infection. Efficacy dose 50 ($ED_{50}$) was calculated by Reed and Muench method (Reed, L. J.; Muench, H. "A simple method of estimating fifty percent endpoints". The American Journal of Hygiene, 1938, 27: 493-497.).

Neutropenic Mice Thigh Infection Model (Human Adapted Model)

Female Swiss Albino mice weighing 24-30 g were used for all studies. Study protocols were reviewed and approved by Institutional Animal Ethical Committee, Orchid Research Laboratories Limited. Mice were rendered neutropenic by intra-peritoneal cyclophosphamide injections. Log phase culture in brain heart infusion broth was injected in to mice thighs. Imipenem or Doripenen alone or in combination were administered sub-cutaneously in decreasing fractionated doses every 15 minutes over the period of 5.5 h (Flückiger, U. et al. "Integration of pharmacokinetics and pharmacodynamics of Imipenem in a human-adapted mouse model'. Antimicrobial Agents and Chemother, 1991, 35(9): 1905-1910). The Compound-1 or tazobactam was administered sub-cutaneously as bolus dose at the start of dosing. Efficacy end point was 6 h in Imipenem studies and 8 h in Doripenen studies.

Efficacy of Piperacillin Restored by Compound-1 Against KPC2 K. Pneumoniae ATCC BAA 1705 in Mice Systemic Infection Model Piperacillin alone was not efficacious up to 800 mg/kg. The Compound-1 restored the efficacy of piperacillin as piperacillin demonstrated an $ED_{50}$ of 50 mg/kg in combination with Compound-1 at 1:1 ratio. As Compound-1 alone was not efficacious, piperacillin efficacy in combination was attributed to KPC2 enzyme inhibitory activity of Compound-1. The clinically used tazobactam however could not restore the piperacillin efficacy as its combination with piperacillin at 1:1 ratio up to >200:>200 mg/kg did not show efficacy (Table 10).

TABLE 10

Comparison of efficacy of piperacillin in combination with Compound-1 versus tazobactam

| Dose group | $ED_{50}$ (mg/kg) |
|---|---|
| Piperacillin | >800 |
| Compound-1 | >64 |
| Tazobactam | >200 |
| Piperacillin:Compound-1 at 1:1 ratio | 50:50 |
| Piperacillin:Tazobactam at 1:1 ratio | >200:>200 |

Efficacy of Imipenem enhanced by Compound-1 Against KPC2 K. pneumoniae ATCC BAA 1705 in Mice Systemic Infection Model Imipenem alone showed an $ED_{50}$ of 8.9 mg/kg. Combining compound-1 at fixed 64 mg/kg resulted in enhancement of efficacy with $ED_{50}$ of 2.2 mg/kg. Addition of tazobactam at same dose with Imipenem resulted in $ED_{50}$ of 4 mg/kg.

Significant increase in efficacy of Imipenem by compound-1 was due to its inhibitory activity on KPC2 enzyme (Table 11).

TABLE 11

Comparison of efficacy of Imipenem in combination with Compound-1 versus tazobactam

| Dose group | $ED_{50}$ (mg/kg) |
| --- | --- |
| Imipenem | 8.9 |
| Imipenem + Compound-1 (64 mg/kg) | 2.2 |
| Imipenem + Tazobactam (64 mg/kg) | 4 |

Efficacy of Doripenen enhanced by Compound-1 against KPC2 K. pneumoniae ATCC BAA 1705 in Mice Systemic Infection Model Doripenem alone and Doripenen in combination with compound-1 or tazobactam were evaluated. The compound-1 or tazobactam were tested at 20 mg/kg and 64 mg/kg. Doripenem alone showed an $ED_{50}$ of 14.14 mg/kg. Its efficacy was significantly enhanced by compound-1 at 20 mg/kg with an $ED_{50}$ of 1.4 mg/kg and at 64 mg/kg with an $ED_{50}$ of 1.62 mg/kg. Tazobactam improved the efficacy of Doripenen marginally with an $ED_{50}$ of 11.89 mg/kg and 6.48 mg/kg at tazobactam doses of 20 and 64 mg/kg respectively (Table 12)

These results suggest the potent inhibitory activity of compound-1 on KPC2 resulting in protection of Doripenen form KPC2 mediated hydrolysis thus restoring the efficacy of Doripenen.

TABLE 12

Comparison of efficacy of Doripenen in combination with Compound-1 versus tazobactam

| Dose group | $ED_{50}$ (mg/kg) |
| --- | --- |
| Doripenem | 14.14 |
| Doripenem + Compound-1 (20 mg/kg) | 1.4 |
| Doripenem + Compound-1 (64 mg/kg) | 1.62 |
| Doripenem + Tazobactam (20 mg/kg) | 11.89 |
| Doripenem + Tazobactam (64 mg/kg) | 6.48 |

Efficacy of Imipenem enhanced by Compound-1 against KPC2 K. pneumoniae ATCC BAA 1705 in Neutropenic Mice Thigh Infection Model The mean initial bacterial load at the start of therapy was 1.8E+06 CFU/thigh. Imipenem 140 mg/kg administered as fractionated doses over the period of 5.5 h was not efficacious; bacteria grew to 6.8E+06 CFU/thigh after 6 h of therapy. Combining to Imipenem with compound-1 at 140 mg/kg as bolus dose restored the efficacy as bacterial load reduced to 2.1E+05 CFU/thigh (Table 13). This experimental result showed that compound-1 demonstrated inhibitory potential in the tough mice thigh infection model.

TABLE 13

In vivo pharmacodynamics (Thigh infection model) of Imipenem in combination with Compound-1

| Dose group | Bacterial load (CFU/thigh) |
| --- | --- |
| Initial bacterial load | 1.81E+06 |
| Infection control | 4.6E+07 |
| Imipenem 140 mg/kg treated | 6.8E+06 |
| Imipenem (140 mg/kg) + Compound-1 (140 mg/kg) | 2.1E+05 |

Efficacy of Doripenem Enhanced by Compound-1 Against KPC2 K. pneumoniae ATCC BAA 1705 in Neutropenic Mice Thigh Infection Model Three experiments were carried out where Doripenen alone or in combination with compound-1 or tazobactam (two experiments) were evaluated. Doripenem 70 mg/kg was administered in fractionated doses over the period of 5.5 h (Fluckiger, U. et al. "Integration of pharmacokinetics and pharmacodynamics of Imipenem in a human-adapted mouse model'. Antimicrobial Agents and Chemother., 1991, 35(9): 1905-1910). Compound-1 or tazobactam was administered as bolus dose at initiation of therapy. Efficacy end point was 8 h after initiation of therapy.

The initial bacterial load ranged from 1.4E+07-3.1E+07 CFU/thigh. Doripenem 70 mg/kg alone exerted a static effect on the bacterial load. Mice treated with Doripenen alone showed bacterial load of 5.4E+06-2.6E+07 CFU/thigh. Combining compound-1 at 35 mg/kg with Doripenen brought the bacterial load down to 7.9E+05-1.3E+06 CFU/thigh. Doripenem was also combined with tazobactam at 35 mg/kg in two experiments. Tazobactam did not have impact on efficacy of Doripenen as mice showed bacterial load of 1.2 E+07-1.6E+07 CFU/thigh (Table 14).

TABLE 14

In vivo pharmacodynamics (Thigh infection model) of Doripenem in combination with Compound-1

| Dose group | Bacterial load (range) (CFU/thigh) |
| --- | --- |
| Initial bacterial load | 1.4E+07-3.1E+07 |
| Infection control | 7.3E+07-1.6E+08 |
| Doripenem 70 mg/kg treated | 5.4E+06-2.6E+07 |
| Doripenem (70 mg/kg) + Compound-1 (35 mg/kg) | 7.9E+05-1.4E+06 |
| Doripenem (70 mg/kg) + Tazobactam (35 mg/kg) | $1.19 \times 10^7$-$1.6 \times 10^7$ |

CONCLUSION

In all these experiments, efficacy of β-lactams as single agents deteriorated as they were not stable to KPC2. Being an inhibitor of KPC2, compound-1 restored or significantly enhanced the efficacy of β-lactams.

We claim:

1. A method of treating a carbapenemase-producing bacterial infection in a subject in need thereof comprising administering to the subject a therapeutically effective amount of one or more antibiotics and a compound of formula (I)

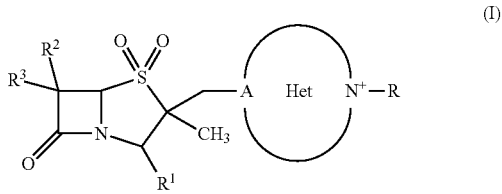

or tautomeric forms, stereoisomers, polymorphs, solvates, hydrates, pharmaceutically acceptable salts and esters thereof, thereby treating the carbapenemase-producing bacterial infection, wherein:

A=C or N;

Het is a substituted three- to seven-membered heterocyclic ring;

R¹ represents a carboxylate anion or —COOR⁴, wherein R⁴ represents hydrogen, $C_1$-$C_6$alkyl, $C_6$-$C_{10}$aryl, $C_6$-$C_{10}$aryl$C_1$-$C_6$alkyl, methoxybenzyl, nitrobenzyl, silyl, diphenylmethyl, or a pharmaceutically acceptable salt;

R² and R³ may be same or different and independently represent hydrogen, halogen, amino, protected amino or optionally substituted $C_1$-$C_6$alkyl, $C_2$-$C_6$ alkenyl or $C_2$-$C_6$ alkynyl;

R represents a substituted or unsubstituted $C_1$-$C_6$ alkyl, $C_2$-$C_6$alkenyl, $C_6$-$C_{10}$aryl, $C_6$-$C_{10}$aryl$C_1$-$C_6$alkyl, $C_3$-$C_{12}$cycloalkyl, oxo, heterocyclyl or heterocyclylalkyl group; and when the groups R, R² and R³ are substituted, the substituents which may be one or more are selected from lower alkyl; lower alkoxy; lower alkylthio; lower alkylamino; cyclo(lower)alkyl; cyclo(lower)alkenyl; hydroxy; halogen; amino; protected amino; cyano; nitro; carbamoyl; —CONH$C_1$-$C_4$alkyl-COO—$C_1$-$C_4$alkyl; carboxy; protected carboxy; —COO—$C_1$-$C_4$alkyl; —CO-heterocyclyl; sulfonyl; sulfamoyl; imino; oxo; amino(lower)alkyl; halo(lower)alkyl; and carboxylic acid and carboxylic acid derivatives, wherein the carbapenemase produced by the carbapenemase-producing bacteria is KPC.

2. The method of claim 1, wherein the compound is of formula (II)

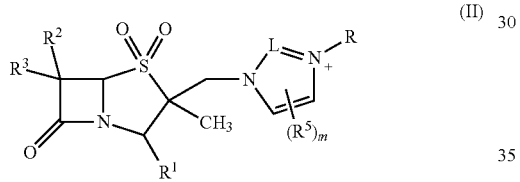

(II)

or tautomeric forms, stereoisomers, polymorphs, solvates, hydrates, pharmaceutically acceptable salts and esters thereof, wherein:

L=C or N;

R¹ represents a carboxylate anion or —COOR⁴, wherein R⁴ represents hydrogen, $C_1$-$C_6$alkyl, $C_6$-$C_{10}$aryl, $C_6$-$C_{10}$aryl$C_1$-$C_6$alkyl, methoxybenzyl, nitrobenzyl, silyl, diphenylmethyl, proxetil, axetil, cilexetil, pivoxil, hexetil, daloxate or a pharmaceutically acceptable salt;

R² and R³ may be same or different and independently represent hydrogen, halogen, amino, protected amino, optionally substituted $C_1$-$C_6$alkyl, $C_2$-$C_6$alkenyl or $C_2$-$C_6$alkynyl;

R represents a substituted or unsubstituted $C_1$-$C_6$ alkyl, $C_2$-$C_6$alkenyl, $C_6$-$C_{10}$aryl, $C_6$-$C_{10}$aryl $C_1$-$C_6$alkyl, $C_3$-$C_{12}$cycloalkyl, oxo, heterocyclyl or heterocyclylalkyl;

R⁵ is hydrogen, $C_1$-$C_6$alkyl, $C_1$-$C_6$alkoxy, $C_1$-$C_6$alkylthio, $C_1$-$C_6$alkylamino, hydroxyl, halogen or trihalomethyl; and m is 0, 1 or 2.

3. The method of claim 1, wherein the compound is selected from:

1-{[(2S,3 S,5R)-2-Carboxy-3-methyl-4,4,7-trioxo-4-thia-1-azabicyclo[3.2.0]hept-3-yl]methyl}-3-methyl-1H-1,2,3-triazol-3-ium;

1-{[(2S,3 S,5R)-2-Carboxy-3-methyl-4,4,7-trioxo-4-thia-1-azabicyclo[3.2.0]hept-3-yl]methyl}-3-ethyl-1H-1,2,3-triazol-3-ium;

1-{[(2S,3 S,5R)-2-Carboxy-3-methyl-4,4,7-trioxo-4-thia-1-azabicyclo[3.2.0]hept-3-yl]methyl}-3-n-propyl-1H-1,2,3-triazol-3-ium;

1-{[(2S,3 S,5R)-2-Carboxy-3-methyl-4,4,7-trioxo-4-thia-1-azabicyclo[3.2.0]hept-3-yl]methyl}-3-allyl-1H-1,2,3-triazol-3-ium;

1-{[(2S,3 S,5R)-2-Carboxy-3-methyl-4,4,7-trioxo-4-thia-1-azabicyclo[3.2.0]hept-3-yl]methyl}-3-(2-amino-2-oxoethyl)-1H-1,2,3-triazol-3-ium and the corresponding acid;

1-{[(2S,3 S,5R)-2-Carboxy-3-methyl-4,4,7-trioxo-4-thia-1-azabicyclo[3.2.0]hept-3-yl]methyl}-3-(2-t-butoxy-2-oxoethyl)-1H-1,2,3-triazol-3-ium and the corresponding acid;

1-{[(2S,3 S,5R)-2-Carboxy-3-methyl-4,4,7-trioxo-4-thia-1-azabicyclo[3.2.0]hept-3-yl]methyl}-3-(2-morpholin-4-yl-2-oxoethyl)-1H-1,2,3-triazol-3-ium and the corresponding acid;

1-{[(2S,3 S,5R)-2-Carboxy-3-methyl-4,4,7-trioxo-4-thia-1-azabicyclo[3.2.0]hept-3-yl]methyl}-3-{2[(2-ethoxy-2-oxoethyl)amino]-2-oxoethyl}-1H-1,2,3-triazol-3-ium and the corresponding acid;

1-{[(2S,3 S,5R)-2-Carboxy-3-methyl-4,4,7-trioxo-4-thia-1-azabicyclo[3.2.0]hept-3-yl]methyl}-3-{2-[(3-ethoxy-3-oxopropyl)amino]-2-oxoethyl}-1H-1,2,3-triazol-3-ium and the corresponding acid;

1-{[(2S,3 S,5R)-2-Carboxy-3-methyl-4,4,7-trioxo-4-thia-1-azabicyclo[3.2.0]hept-3-yl]methyl}-3-(2-{[1-(ethoxycarbonyl)-2-hydroxypropyl]amino}-2-oxoethyl)-1H-1,2,3-triazol-3-ium and the corresponding acid;

1-{[(2 S,3 S,5R)-2-Carboxy-3-methyl-4,4,7-trioxo-4-thia-1-azabicyclo[3.2.0]hept-3-yl]methyl}-3-benzyl-1H-1,2,3-triazol-3-ium and the corresponding acid;

(2 S,3 S,5R)-3-Methyl-3-(3-methyl-imidazol-3-ium-1-ylmethyl)-4,4,7-trioxo-4-thia-1-azabicyclo[3.2.0]heptane-2-carboxylate and the corresponding acid;

(2 S,3 S,5R)-3-Methyl-3-(4-methyl-3-methyl-imidazol-3-ium-1-ylmethyl)-4,4,7-trioxo-4-thia-1-aza-bicyclo [3.2.0]heptane-2-carboxylate or corresponding acids, tautomeric forms, stereoisomers, polymorphs, solvates, hydrates, pharmaceutically acceptable salts and esters thereof.

4. The method of claim 1, wherein the compound is, 1-{[(2S,3 S,5R)-2-Carboxy-3-methyl-4,4,7-trioxo-4-thia-1-azabicyclo[3.2.0]hept-3-yl]methyl}-3-methyl-1H-1,2,3-triazol-3-ium or tautomeric forms, stereoisomers, polymorphs, solvates, hydrates, pharmaceutically acceptable salts and esters thereof.

5. A method of treating a carbapenemase-producing bacterial infection comprising administering a pharmaceutical composition comprising the compound of formula (I) as defined according to claim 1, or a pharmaceutically acceptable salt thereof, one or more antibiotics and a pharmaceutically acceptable carrier, thereby treating the carbapenemase-producing bacterial infection, wherein the carbapenemase produced by the carbapenemase-producing bacteria is KPC.

6. The method of claim 5, wherein the antibiotics are β-lactam antibiotics.

7. The method of claim 6, wherein the antibiotics are selected from the group consisting of Penicillins, Cephalosporins, Carbacephem, Oxacephem, Carbapenems, Cephamycins, Penems, Monobactams or a combination thereof.

8. The method of claim 7, wherein the penicillins are selected from the group consisting of Amdinocillin (Mecillinam), Amoxicillin, Ampicillin, Amylpenicillin, Apalcillin, Aspoxicillin, Azidocillin, Azlocillin, Bacampicillin, Carbenicillin, Carindacillin, Clometocillin, Cloxacillin, Cyclacillin (Ciclacillin), Dicloxacillin, Epicillin, Fenbenicillin, Floxacillin (flucloxacillin), Hetacillin, Lenampicillin, Metampicillin, Methicillin, Mezlocillin, Nafcillin, Oxacillin, Penamecillin, Penethecillin, Penicillin G (Procaine Penicillin), Penicillin N, Penicillin O, Penicillin V (Phenoxymethyl Penicillin), Phenethicillin, Piperacillin, Pivampicillin, Propicillin, Quinacillin, Sulbenicillin, Talampicillin, Temocillin, Ticarcillin, Pivmecillinam, Benzathine Penicillin, Benzyl Penicillin, Co-amoxiclav and Lenampicillin.

9. The method of claim 7, wherein the cephalosporins are selected from the group consisting of Cephaloridin, Cephradine, Cefoxitin, Cephacetril, Cefinenoxime, Cephaloglycin, Cefonicid, Cefodizime, Cefpirome, Cefpiramide, Cefozopran, Cefoselis, Cefluprenam, Cefpimizole, Cefclidin, Cefpodoxime axetil, Cefteram pivoxil, Cefcapene pivoxil, Ceftobiprole, Ceftaroline, Cefoperazone, Cefquinome, Ceftiofur, Cefovecin, Cefadroxil, Cefalonium, Cefepime, Cefotaxime, Ceftazidime, Cefetamet pivoxil, Cefditoren pivoxil, Cephaloridine, Ceftazidime, Ceftriaxone, Cefbuperazone, Cephalothin, Cephazolin, Cephapirin, Ceftezole, Cefamandole, Cefotiam, Cefotiam hexetil, Cefuroxime, Ceftizoxime, Cefmenoxime, Cefuzonam, Cefsulodin, Cefmetazole, Cefminox, Cephalexin, Cefradine, Cefaclor, Cefadroxil, Cefalonium, Cefprozil, Cefuroxime axetil, Cefixime, Cefpodoxime proxetil, Ceftibuten, CXA-101 (FR264205), and Cefdinir.

10. The method of claim 7, wherein the carbapenems are selected from the group consisting of Meropenem, Ertapenem, Doripenem, Biapenem, Panipenem, Ritipenem, Tebipenem, Tomopenem, Sulopenem, Razupenem, Imipenem, ME1036 and SM216601.

11. The method of claim 7, wherein the Monobactams are selected from the group consisting of Aztreonam, Carumonam, Tigemonam, BAL19764 and BAL30072.

12. The method of claim 5, wherein the antibiotics are selected from the group consisting of Imipenem, Faropenem, Doripenem, Meropenem, Ertapenem, Aztreonam, Cefepime, Cefotaxime, Ceftazidime, Ceftobiprole, Cefquinome, Ceftiofur, Cefadroxil and Cefalonium.

13. A method for detecting carbapenemases comprising administering a diagnostic reagent to a sample, wherein the diagnostic reagent comprises the compound of formula (I) as defined according to claim 1, wherein the carbapenemases belong to the families of KPC.

14. The method of claim 5, wherein the antibiotic is selected from the group consisting of Penicillins, Cephalosporins, Penems, Carbacephem, Carbapenems, Oxacephem, Monobactams, Aminoglycosides, Bacteriocins, Quinolones, Sulfonamides, Macrolides, Tetracyclines, Glycylcyclines, Oxazolidinones, Lipopeptides, Polypeptides, Rifamycins, Chloramphenicol, Polyene antifungals and derivatives thereof.

15. A method for restoring and/or potentiating the activity of antibiotics in a subject by inhibiting carbapenemases produced by bacteria comprising administering a therapeutically effective amount of the compound of formula (I) as defined according to claim 1, or a pharmaceutically acceptable salt thereof, to a subject in need thereof, wherein the carbapenemases produced by the bacteria are KPC.

16. The method of claim 15, wherein the antibiotics are selected from the group consisting of Penicillins, Cephalosporins, Carbacephem, Oxacephem, Carbapenems, Cephamycins, Penems, Monobactams or a combination thereof.

17. The method of claim 1, wherein the one or more antibiotics are administered separately from the compound of formula (I).

18. The method of claim 1, wherein the carbapenemase-producing bacteria are Gram-negative bacteria.

19. The method of claim 1, wherein the subject is selected from the group consisting of patients with bacterial infections, preoperative patients, postoperative patients, patients in ICU, patients with nosocomial infections, patients with community acquired infections and veterinaries.

* * * * *